US010987369B2

(12) United States Patent
Yang et al.

(10) Patent No.: US 10,987,369 B2
(45) Date of Patent: Apr. 27, 2021

(54) PDIA4 PROTEIN AS A TARGET FOR DIAGNOSIS, MONITORING AND TREATMENT OF DIABETES

(71) Applicant: ACADEMIA SINICA, Taipei (TW)

(72) Inventors: Wen-Chin Yang, Taichung County (TW); Lee-Tian Chang, Taichung (TW)

(73) Assignee: ACADEMIA SINICA, Taipei (TW)

( * ) Notice: Subject to any disclaimer, the term of this patent is extended or adjusted under 35 U.S.C. 154(b) by 257 days.

(21) Appl. No.: 15/302,938

(22) PCT Filed: Apr. 9, 2015

(86) PCT No.: PCT/US2015/025015
§ 371 (c)(1),
(2) Date: Oct. 7, 2016

(87) PCT Pub. No.: WO2015/157476
PCT Pub. Date: Oct. 15, 2015

(65) Prior Publication Data
US 2017/0049794 A1 Feb. 23, 2017

Related U.S. Application Data

(60) Provisional application No. 61/977,835, filed on Apr. 10, 2014.

(51) Int. Cl.
| | |
|---|---|
| *A61K 31/7028* | (2006.01) |
| *A61K 38/43* | (2006.01) |
| *A61K 31/7105* | (2006.01) |
| *A61K 31/341* | (2006.01) |
| *A61K 31/216* | (2006.01) |
| *A61K 31/235* | (2006.01) |
| *A61K 31/58* | (2006.01) |
| *A61K 31/155* | (2006.01) |
| *A61K 31/4439* | (2006.01) |
| *A61K 45/06* | (2006.01) |
| *C12N 15/113* | (2010.01) |
| *G01N 33/68* | (2006.01) |

(52) U.S. Cl.
CPC ........ *A61K 31/7028* (2013.01); *A61K 31/155* (2013.01); *A61K 31/216* (2013.01); *A61K 31/235* (2013.01); *A61K 31/341* (2013.01); *A61K 31/4439* (2013.01); *A61K 31/58* (2013.01); *A61K 31/7105* (2013.01); *A61K 38/43* (2013.01); *A61K 45/06* (2013.01); *C12N 15/113* (2013.01); *G01N 33/6893* (2013.01); *C12N 2310/14* (2013.01); *C12N 2320/30* (2013.01); *G01N 2333/99* (2013.01); *G01N 2500/04* (2013.01); *G01N 2800/042* (2013.01)

(58) Field of Classification Search
CPC .............. A61K 31/7028; A61K 31/155; A61K 31/4439; A61K 45/06; C12N 15/113; C12N 2310/14; C12N 2320/30; G01N 33/6893; G01N 2333/99; G01N 2500/04; G01N 2800/042
USPC ......................................................... 514/25
See application file for complete search history.

(56) References Cited

U.S. PATENT DOCUMENTS

| | | | | |
|---|---|---|---|---|
| 2005/0260709 | A1* | 11/2005 | Andag | ............... C07K 14/5759 435/69.1 |
| 2011/0229702 | A1 | 11/2011 | Yang | |
| 2011/0280809 | A1 | 11/2011 | Yang | |

FOREIGN PATENT DOCUMENTS

WO 2009117196 A1 9/2009

OTHER PUBLICATIONS

Kumar et al. (Chem. Eur. J. 2011, 17, 8696-8703).*
Fonseca et al. (JAMA, Apr. 5, 2000, vol. 283, No. 13, 1695)-1702).*
Cnop et al. (Trends in Molecular Medicine, Jan. 2012, vol. 18, No. 1, 59-68).*
Tufo et al. (Cell Death and Differentiation (2014) 21, 685-695).*
Chang et al. (Evidence-Based Complementary and Alternative Medicine, vol. 2013, Article ID 685642, 13 pages; Published online Mar. 13, 2013).*
Of Chang et al. (The Journal of Immunology, 2007, 178: 6984-6993).*
International Search Report for PCT/US2015/025015, dated Oct. 8, 2015.
Written Opinion of International Search Authority for PCT/US2015/025015, dated Oct. 8, 2015.

* cited by examiner

*Primary Examiner* — Shaojia A Jiang
*Assistant Examiner* — Michael C Henry
(74) *Attorney, Agent, or Firm* — Hsiu-Ming Saunders; Intellectual Property

(57) ABSTRACT

A Pdia4 inhibitor for use in preventing, alleviating and/or treating diabetes and/or diabetes-related complications in a subject in need thereof is disclosed, wherein the Pdia4 inhibitor does not comprise cytopiloyene. A Pdia4 inhibitor and one other anti-diabetic agent for use in combination therapy in preventing, alleviating, treating diabetes and diabetes-related complications, and/or reversing diabetes in a subject in need thereof is also disclosed, wherein the Pdia4 inhibitors for use in combination therapy may comprise cytopiloyene. Also disclosed are methods for diagnosing, treating and monitoring diabetes, and methods of screening for a Pdia4 inhibitor and/or an anti-diabetic agent.

8 Claims, 9 Drawing Sheets

Specification includes a Sequence Listing.

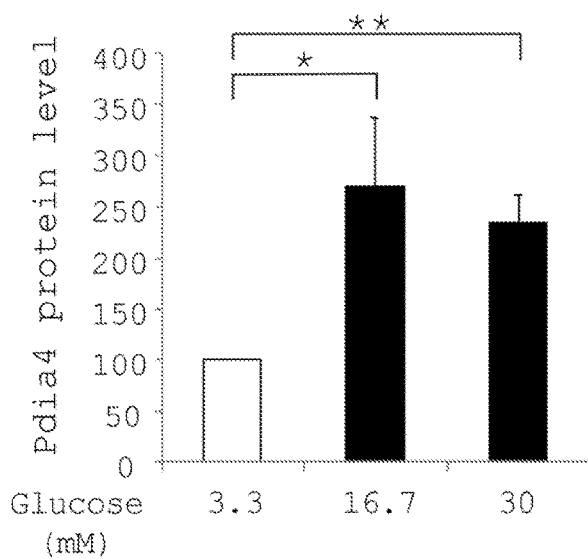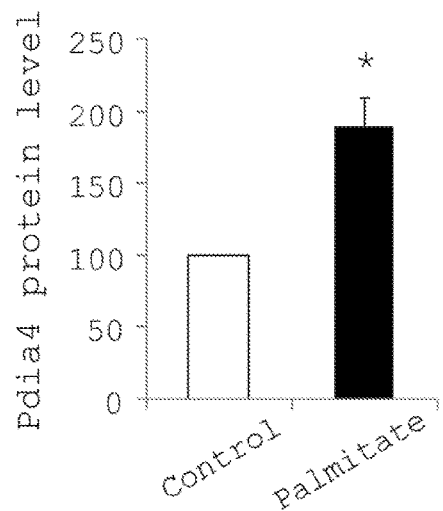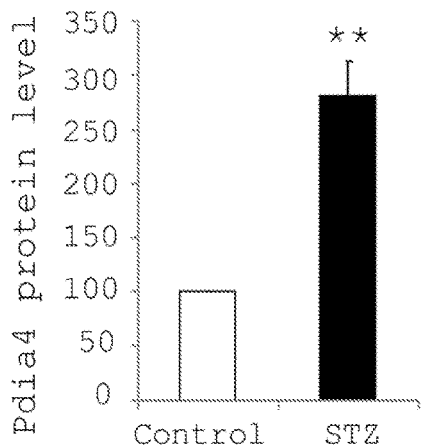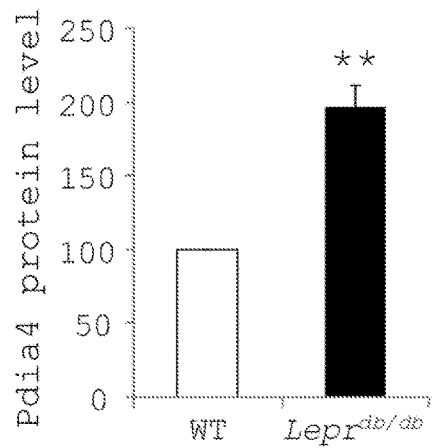
*, P<0.05, , P<0.01, *, P<0.001

FIG. 6A
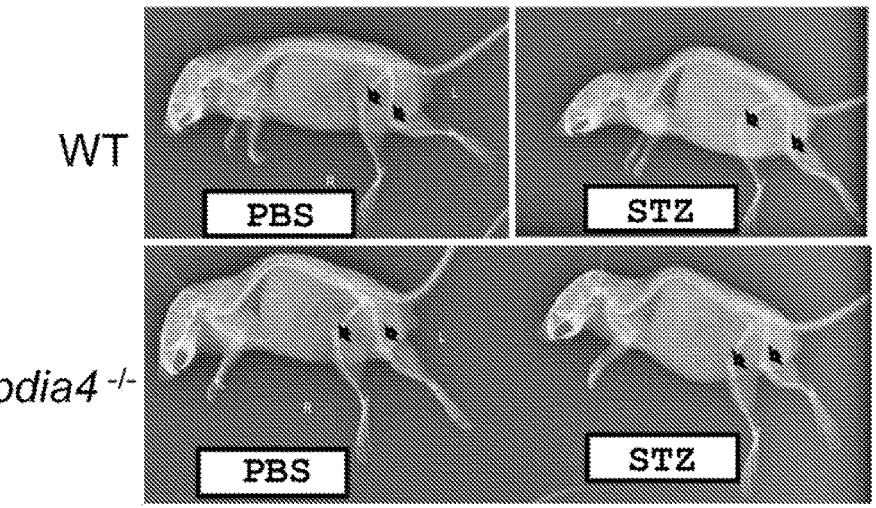
FIG. 6B
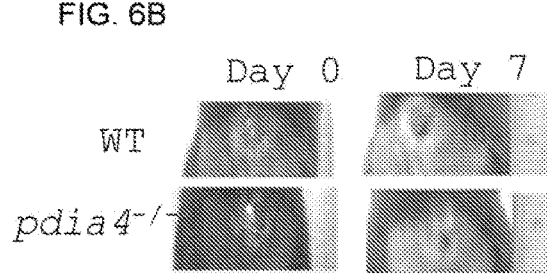
FIG. 6C
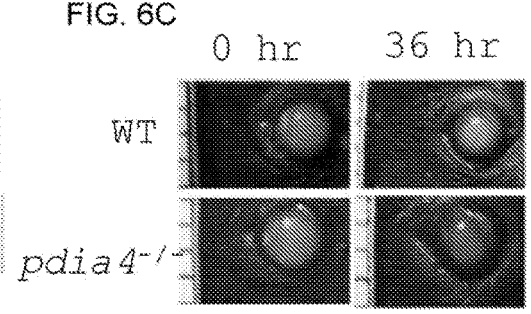
FIG. 6D
|  | $Lepr^{db/db}$ | $pdia4^{-/-} lepr^{db/db}$ |
|---|---|---|
| Creatinine clearance ratio (ml/min) | 24.2 ± 1.0 | 118.7 ± 16.4 |
FIG. 6E
|  | $Lepr^{db/db}$ | $pdia4^{-/-} lepr^{db/db}$ |
|---|---|---|
| Serum triglyceride (mg/dL) | 65.3 ± 17.8 | 30.2 ± 4.1 |
| Serum HDL (mg/dL) | 98.1 ± 7.5 | 136.8 ± 9.9[b] |

FIG. 8A
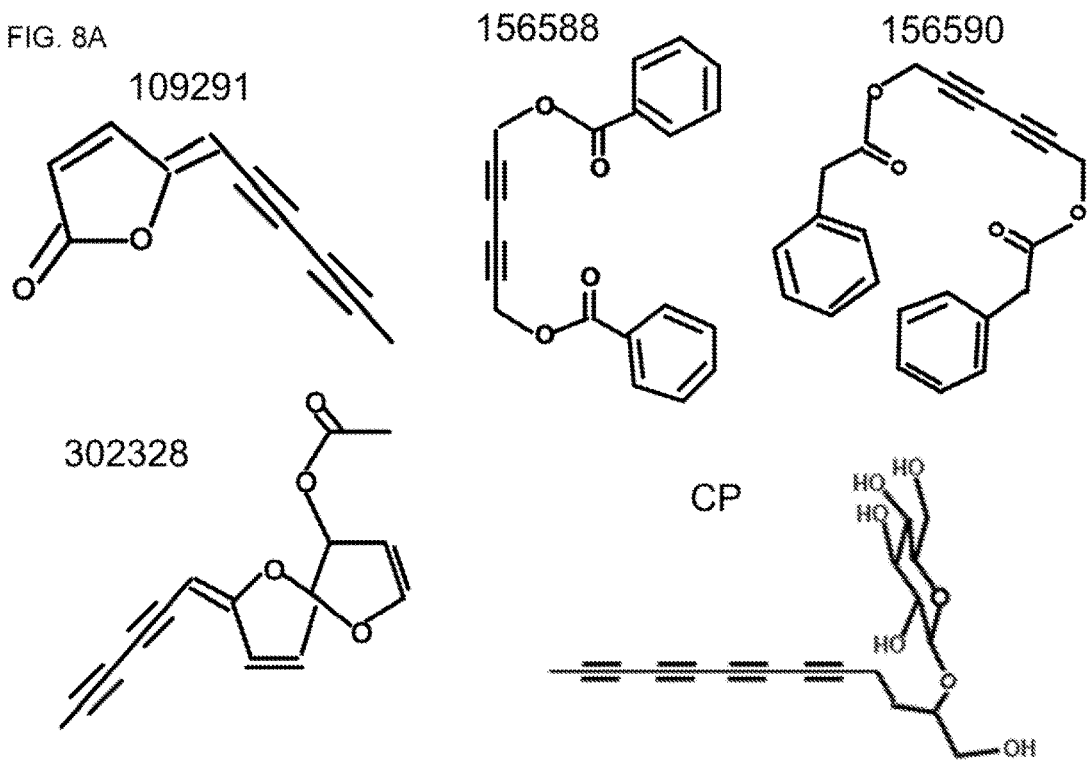
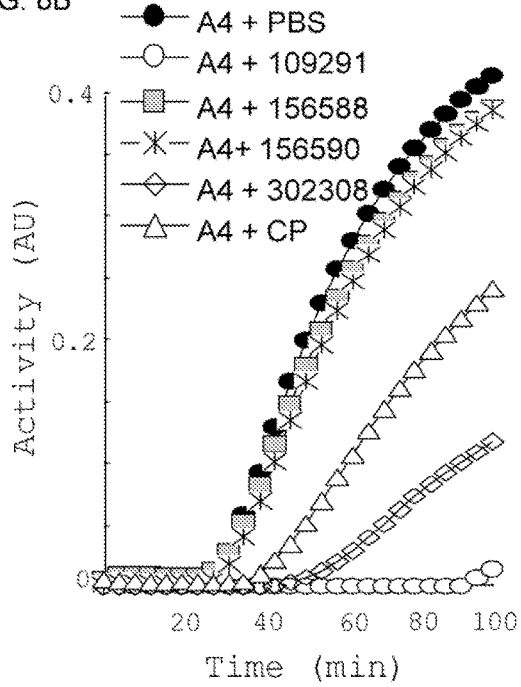
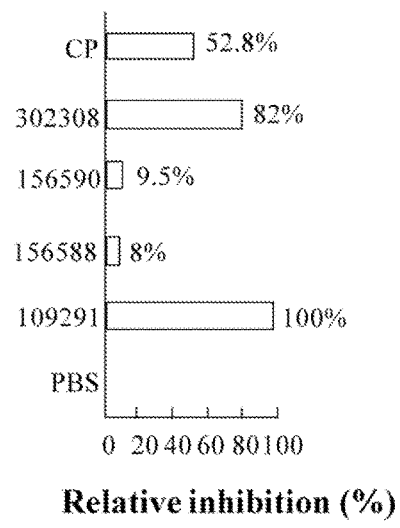

SEQUENCE LISTING

```
<160> NUMBER OF SEQ ID NOS: 5

<210> SEQ ID NO 1
<211> LENGTH: 58
<212> TYPE: DNA
<213> ORGANISM: Artificial Sequence
<220> FEATURE:
<223> OTHER INFORMATION: shRNA

<400> SEQUENCE: 1
ccgggcttgt gttgaccaaa gagaactcga gttctctttg gtcaacacaa gcttttg        58

<210> SEQ ID NO 2
<211> LENGTH: 58
<212> TYPE: DNA
<213> ORGANISM: Artificial Sequence
<220> FEATURE:
<223> OTHER INFORMATION: shRNA

<400> SEQUENCE: 2
ccggccaaga agtacaaggg ccaaactcga gtttggccct tgtacttctt ggttttg        58

<210> SEQ ID NO 3
<211> LENGTH: 58
<212> TYPE: DNA
<213> ORGANISM: Artificial Sequence
<220> FEATURE:
<223> OTHER INFORMATION: shRNA

<400> SEQUENCE: 3
ccgggcaagg tgtcaaacga tgctactcga gtagcatcgt tgacaccctt gcttttg        58

<210> SEQ ID NO 4
<211> LENGTH: 58
<212> TYPE: DNA
<213> ORGANISM: Artificial Sequence
<220> FEATURE:
<223> OTHER INFORMATION: shRNA

<400> SEQUENCE: 4
ccggcttggt cctaaatgat gcaaactcga gtttgcatca tttaggacca agttttg        58

<210> SEQ ID NO 5
<211> LENGTH: 645
```

<212> TYPE: PRT
<213> ORGANISM: Homo sapiens

<400> SEQUENCE: 5

```
Met Arg Pro Arg Lys Ala Phe Leu Leu Leu Leu Leu Gly Leu Val
1               5                   10                  15

Gln Leu Leu Ala Val Ala Gly Ala Glu Gly Pro Asp Glu Asp Ser Ser
            20                  25                  30

Asn Arg Glu Asn Ala Ile Glu Asp Glu Glu Glu Glu Glu Glu Asp
            35                  40                  45

Asp Asp Glu Glu Glu Asp Asp Leu Glu Val Lys Glu Glu Asn Gly Val
    50                  55                  60

Leu Val Leu Asn Asp Ala Asn Phe Asp Asn Phe Val Ala Asp Lys Asp
65                  70                  75                  80

Thr Val Leu Leu Glu Phe Tyr Ala Pro Trp Cys Gly His Cys Lys Gln
                85                  90                  95

Phe Ala Pro Glu Tyr Glu Lys Ile Ala Asn Ile Leu Lys Asp Lys Asp
            100                 105                 110

Pro Pro Ile Pro Val Ala Lys Ile Asp Ala Thr Ser Ala Ser Val Leu
        115                 120                 125

Ala Ser Arg Phe Asp Val Ser Gly Tyr Pro Thr Ile Lys Ile Leu Lys
    130                 135                 140

Lys Gly Gln Ala Val Asp Tyr Glu Gly Ser Arg Thr Gln Glu Glu Ile
145                 150                 155                 160

Val Ala Lys Val Arg Glu Val Ser Gln Pro Asp Trp Thr Pro Pro Pro
                165                 170                 175

Glu Val Thr Leu Val Leu Thr Lys Glu Asn Phe Asp Glu Val Val Asn
            180                 185                 190

Asp Ala Asp Ile Ile Leu Val Glu Phe Tyr Ala Pro Trp Cys Gly His
        195                 200                 205

Cys Lys Lys Leu Ala Pro Glu Tyr Glu Lys Ala Ala Lys Glu Leu Ser
    210                 215                 220

Lys Arg Ser Pro Pro Ile Pro Leu Ala Lys Val Asp Ala Thr Ala Glu
225                 230                 235                 240

Thr Asp Leu Ala Lys Arg Phe Asp Val Ser Gly Tyr Pro Thr Leu Lys
                245                 250                 255

Ile Phe Arg Lys Gly Arg Pro Tyr Asp Tyr Asn Gly Pro Arg Glu Lys
            260                 265                 270

Tyr Gly Ile Val Asp Tyr Met Ile Glu Gln Ser Gly Pro Pro Ser Lys
        275                 280                 285

Glu Ile Leu Thr Leu Lys Gln Val Gln Glu Phe Leu Lys Asp Gly Asp
    290                 295                 300

Asp Val Ile Ile Ile Gly Val Phe Lys Gly Glu Ser Asp Pro Ala Tyr
305                 310                 315                 320

Gln Gln Tyr Gln Asp Ala Ala Asn Asn Leu Arg Glu Asp Tyr Lys Phe
                325                 330                 335
```

```
His His Thr Phe Ser Thr Glu Ile Ala Lys Phe Leu Lys Val Ser Gln
            340                 345                 350

Gly Gln Leu Val Val Met Gln Pro Glu Lys Phe Gln Ser Lys Tyr Glu
            355                 360                 365

Pro Arg Ser His Met Met Asp Val Gln Gly Ser Thr Gln Asp Ser Ala
            370                 375                 380

Ile Lys Asp Phe Val Leu Lys Tyr Ala Leu Pro Leu Val Gly His Arg
385                 390                 395                 400

Lys Val Ser Asn Asp Ala Lys Arg Tyr Thr Arg Arg Pro Leu Val Val
            405                 410                 415

Val Tyr Tyr Ser Val Asp Phe Ser Phe Asp Tyr Arg Ala Ala Thr Gln
            420                 425                 430

Phe Trp Arg Ser Lys Val Leu Glu Val Ala Lys Asp Phe Pro Glu Tyr
            435                 440                 445

Thr Phe Ala Ile Ala Asp Glu Glu Asp Tyr Ala Gly Glu Val Lys Asp
            450                 455                 460

Leu Gly Leu Ser Glu Ser Gly Glu Asp Val Asn Ala Ala Ile Leu Asp
465                 470                 475                 480

Glu Ser Gly Lys Lys Phe Ala Met Glu Pro Glu Glu Phe Asp Ser Asp
            485                 490                 495

Thr Leu Arg Glu Phe Val Thr Ala Phe Lys Lys Gly Lys Leu Lys Pro
            500                 505                 510

Val Ile Lys Ser Gln Pro Val Pro Lys Asn Asn Lys Gly Pro Val Lys
            515                 520                 525

Val Val Val Gly Lys Thr Phe Asp Ser Ile Val Met Asp Pro Lys Lys
            530                 535                 540

Asp Val Leu Ile Glu Phe Tyr Ala Pro Trp Cys Gly His Cys Lys Gln
545                 550                 555                 560

Leu Glu Pro Val Tyr Asn Ser Leu Ala Lys Lys Tyr Lys Gly Gln Lys
            565                 570                 575

Gly Leu Val Ile Ala Lys Met Asp Ala Thr Ala Asn Asp Val Pro Ser
            580                 585                 590

Asp Arg Tyr Lys Val Glu Gly Phe Pro Thr Ile Tyr Phe Ala Pro Ser
            595                 600                 605

Gly Asp Lys Lys Asn Pro Val Lys Phe Glu Gly Gly Asp Arg Asp Leu
            610                 615                 620

Glu His Leu Ser Lys Phe Ile Glu Glu His Ala Thr Lys Leu Ser Arg
625                 630                 635                 640

Thr Lys Glu Glu Leu
            645
```

PDIA4 PROTEIN AS A TARGET FOR DIAGNOSIS, MONITORING AND TREATMENT OF DIABETES

REFERENCE TO RELATED APPLICATION

This application is a national stage application (under 35 U.S.C. 371) of PCT/US2015/025015 filed on 9 Apr. 2015, which claims priority to US provisional application 61/977,835 filed on 10 Apr. 2014, all of which are herein incorporated by reference in their entireties.

FIELD OF THE INVENTION

The present invention relates to the role and use of Pdia4 as a therapeutic target in diabetes.

BACKGROUND OF THE INVENTION

Current anti-diabetic agents, including insulin sensitizers, insulin releasers, α-glucosidase inhibitor, incretin-based drugs (GLP-1 analogues and dipeptidyl peptidase-4 inhibitors), SGLT2 inhibitors and others have been developed to control glucose homeostasis via different mechanisms. However, the above therapeutics can only improve Type 2 diabetes (T2D) symptoms but fails to reverse the disorder. Evidence from human and animal studies suggests that T2D is characterized by reduced functional β-cell mass that cannot adapt insulin secretion to compensate for escalating insulin resistance driving T2D development (FIG. 1). Preclinical and clinical data showed that the β-cell function and mass continued declining, leading to T2D progression. Accumulating data suggest that this decline could be stabilized, delayed and even reversed especially at the early stages of diabetes, raising the possibility that preserving functional mass is essential for preventing and curing T2D. However, no anti-diabetic drugs have clinically been proven effective for preserving β-cell mass and function though TZDs and GLP-1 analogues were reported to prevent β-cell atrophy in preclinical animals.

The family of protein disulfide isomerases (PDIs) play role in mammalian development and diseases. There are 9 PDI members containing 1 to 3 CGHC active sites in human. Among the 9 human PDIs, Pdia-4 is the only PDI member with 3 CGHC motifs. Nothing is known about the gene function of Pdia-4 in cell growth and viability in pancreatic β cells, let alone its role in diabetes.

SUMMARY OF THE INVENTION

The invention relates to the discovery that expression of Pdia4 in β cells was up-regulated in response to metabolic stress. Blood Pdia4 was increased in diabetic animals. Moreover, Pdia4 negatively modulated β-cell function. Conversely, decreasing Pdia4 is protective to β-cells. Pdia4 aggravates diabetes development in mouse models. Strikingly, a combination of β-cell preservation, by Pdia4 inhibition/ablation, and reduction of insulin resistance, by insulin sensitizers, metformin, and metformin/rosiglitazone, could reverse diabetes and reduce diabetic complications in preclinical trials.

In one aspect, the invention relates to use of a therapeutically effective amount of a Pdia4 inhibitor in the manufacture of a medicament for preventing, alleviating and/or treating diabetes and/or diabetes-related complications in a subject in need thereof, wherein the Pdia4 inhibitor inhibits Pdia4 protein activity and/or inhibits Pdia4 protein expression and wherein the use of the Pdia4 inhibitor does not comprise use of a compound of formula (I):

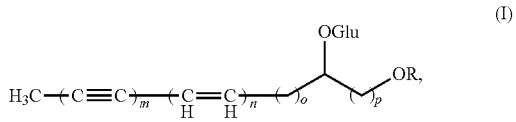

wherein:
R is H or COCH2COOH;
m=3 or 4;
n=0 or 1;
o=2; and
p=1 or 2.

In one embodiment of the invention, the Pdia4 inhibitor is selected from the group consisting of

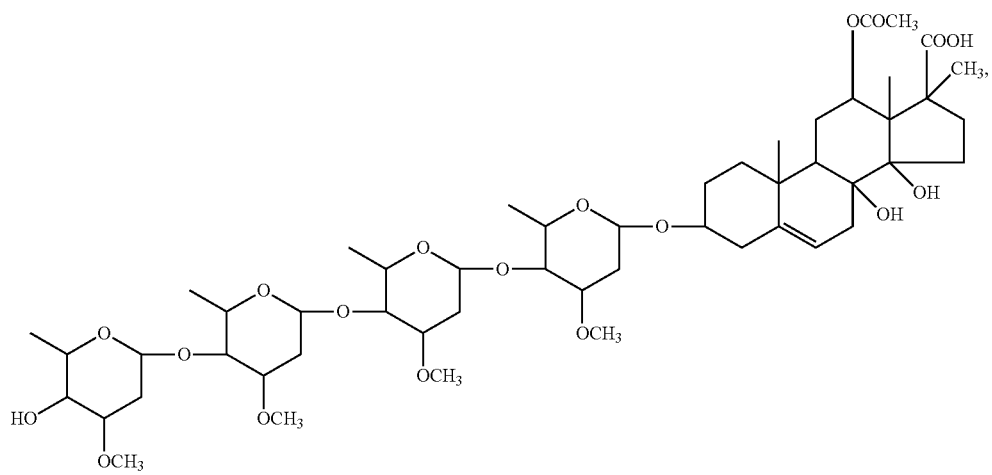

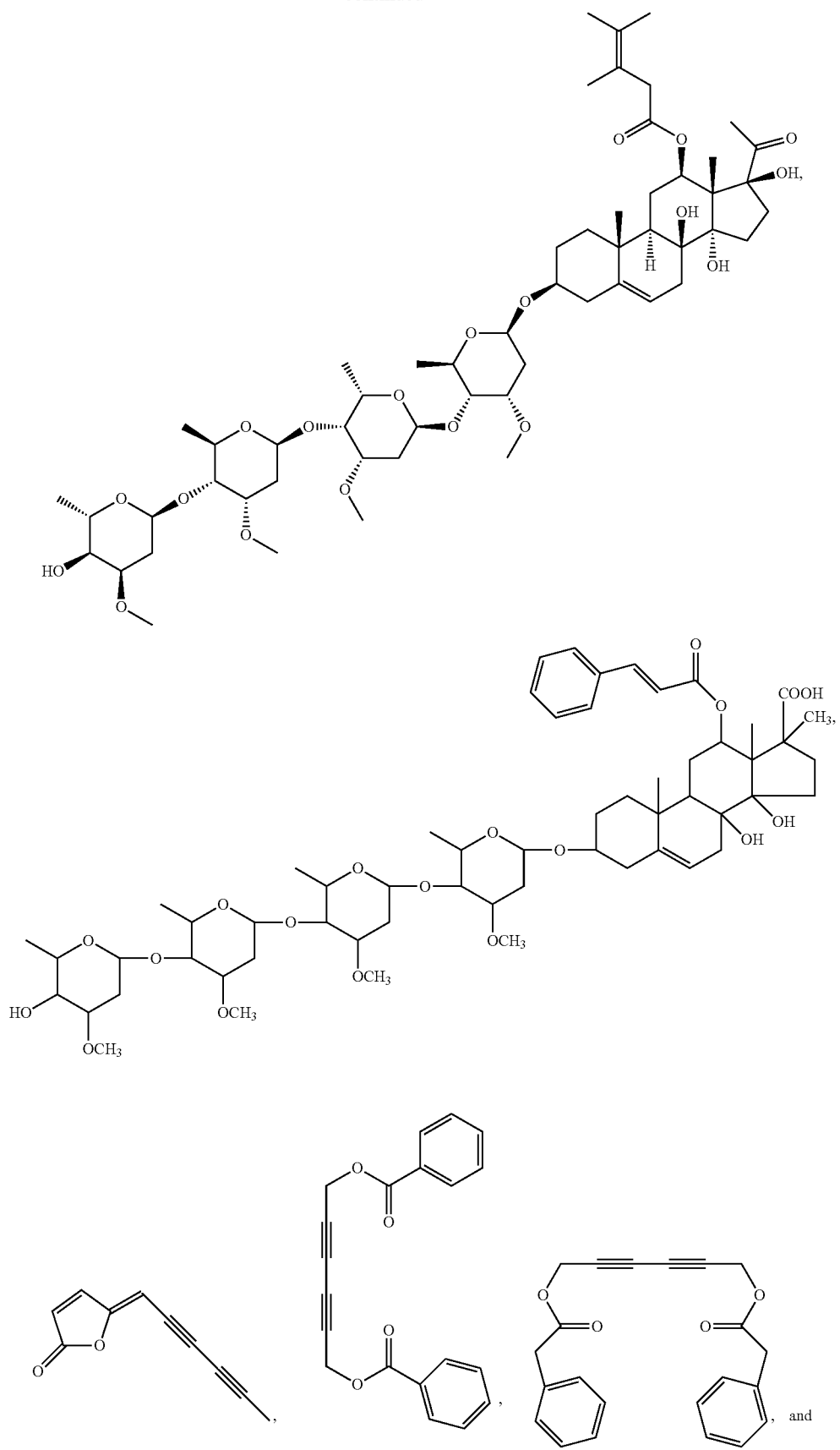

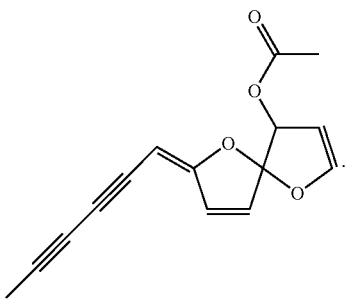

In another aspect, the invention relates to use of a therapeutically effect amount of a Pdia4 inhibitor and use of one other anti-diabetic agent in the manufacture of medicaments for combination therapy for preventing, alleviating, treating diabetes and/or diabetes-related complications, and/or reversing diabetes in a subject in need thereof, wherein the Pdia4 inhibitor inhibits Pdia4 protein activity and/or inhibits Pdia4 protein expression. In one embodiment of the invention as mentioned herein, the use of the Pdia4 inhibitor may comprises use of a compound of formula (I):

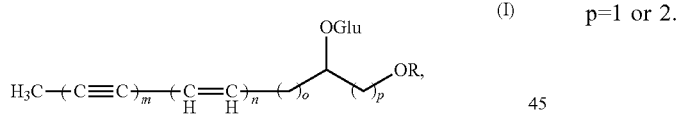

wherein:

R is H or COCH2COOH;

m=3 or 4;

n=0 or 1;

o=2; and p=1 or 2.

In another embodiment of the invention, the Pdia4 inhibitor is a compound selected from the group consisting of

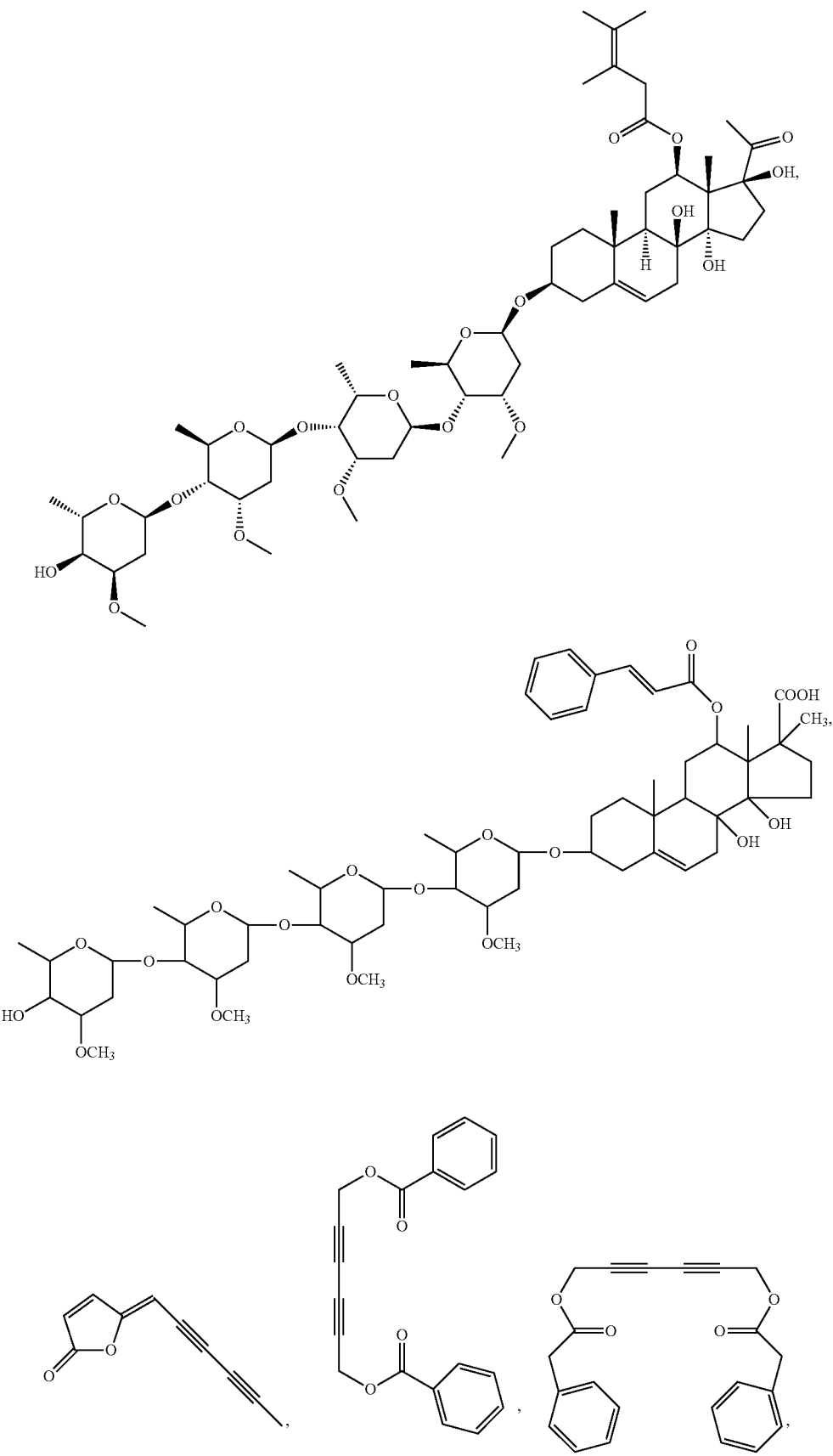

-continued

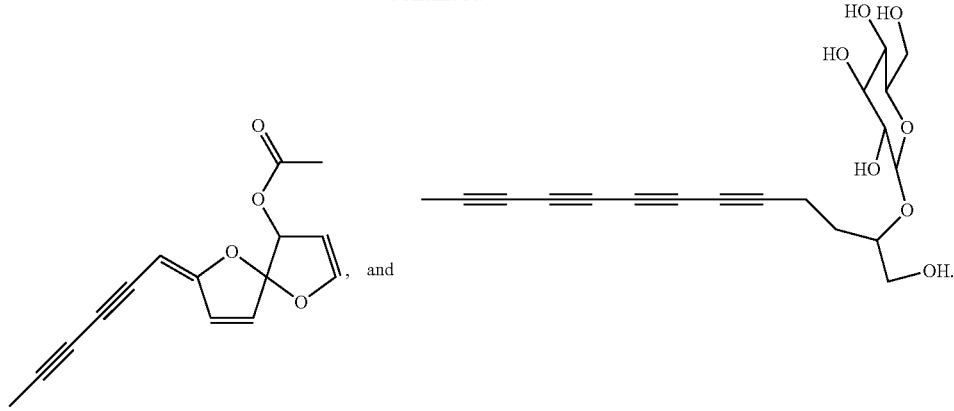
, and

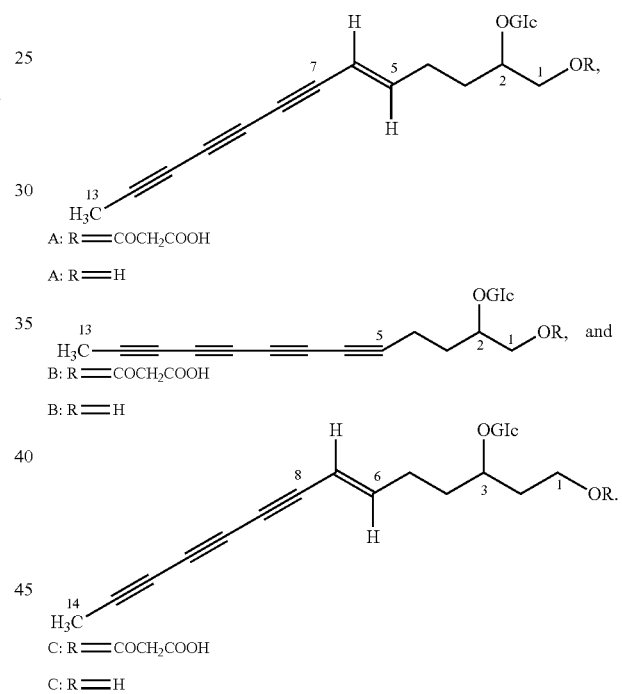

In another embodiment or the invention, the Pdia4 inhibitor inhibits Pdia4 protein expression and is selected from the group consisting of an antisense molecule, a triple helix molecule, a ribozyme and an shRNA.

In another embodiment of the invention, the Pdia4 inhibitor inhibits Pdia4 protein activity and is selected from the group consisting of an anti-Pdia4 antibody, a terpenoid, and a polyyne.

In another embodiment of the invention, the polyyne is a compound of formula (II):

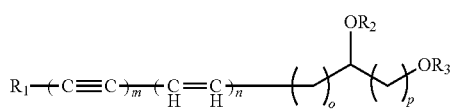

(II)

wherein $R_1$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl;

$R_2$ is H or a monosaccharide residue; $R_3$ is or $C_1$-$C_{10}$ alkyl; m is 2, 3, or 4; n is 0, 1, 2, or 3; o is 0, 1, 2, 3, or 4; and p is 1, 2, 3, or 4.

In another embodiment of the invention, the polyyne is a compound of formula (I):

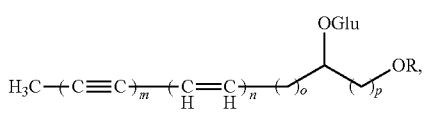

(I)

wherein:

R is H or COCH$_2$COOH;

m=3 or 4;

n=0 or 1;

o=2; and p=1 or 2.

In another embodiment of the invention, the compound of formula (I) is selected from the group consisting of

A: R═COCH$_2$COOH

A: R═H

B: R═COCH$_2$COOH

B: R═H

C: R═COCH$_2$COOH

C: R═H

In another embodiment of the invention, the compound is cytopiloyene.

The terpenoids may be a diterpenoid selected from the group consisting of 12-O-acetyl-8,14-dihydroxy-17-methyl-3-orthenthosyletienic acid, 8,14-dihydroxy-12-O-(4,5-dimethylhexanoyl)-17-methyl-3-orthenthosylpregnenolone, and 12-O-cinnamoyl-8,14-dihydroxy-17-methyl-3-orthenthosyletienic acid.

In another embodiment of the invention, the subject is afflicted with type 2 diabetes.

In another embodiment of the invention, the one other anti-diabetic agent is an insulin sensitizer.

In another embodiment of the invention, the shRNA comprises a nucleotide sequence selected from the group consisting of: SEQ ID NOs: 1-4.

The anti-diabetic agent may be selected from the group consisting of insulin sensitizers (biguanides, PPARγ agonists), glucagon-like peptide 1 (GLP-1) analogues, DPPV inhibitors, sodium/glucose cotransporter 2 (SGLT2) inhibitors, β-glucosidase inhibitors, amylin mimetics, bile acid sequestrants, and dopamine agonists.

The diabetes-related complications include eye disease, cardiovascular disease, kidney disease and foot ulcers.

Alternatively, the invention relates to a therapeutically effective amount of a Pdia4 inhibitor for use in preventing, alleviating and/or treating diabetes and/or diabetes-related complications in a subject in need thereof, wherein the Pdia4 inhibitor inhibits Pdia4 protein activity and/or inhibits Pdia4 protein expression and wherein the Pdia4 inhibitor does not comprise a compound of formula (I):

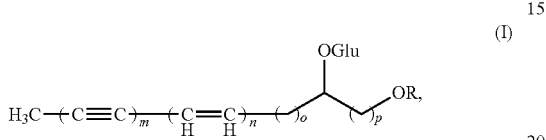

(I)

wherein;
R is H or COCH2COOH;
m=3 or 4;
n=0 or 1;
o=2; and
p=1 or 2.

Alternatively, the invention relates to a method of preventing, alleviatin and/or treating diabetes and/or diabetes-related complications in a subject in need thereof, comprising: administering to the subject a Pdia4 inhibitor in a therapeutically effective amount to alleviate and/or treat the diabetes in the subject, wherein the Pdia4 inhibitor inhibits Pdia4 protein activity and/or inhibits Pdia4 protein expression and wherein the Pdia4 inhibitor does not comprise a compound of formula (I):

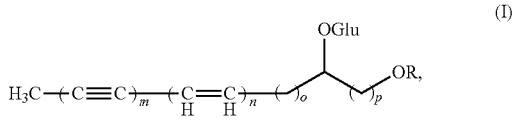

(I)

wherein:
R is H or COCH2COOH;
m=3 or 4;
n=0 or 1;
o=2; and
p=1 or 2.

Alternatively, the invention relates to a therapeutically effect amount of a Pdia4 inhibitor and one other anti-diabetic agent for use in combination therapy in preventing, alleviating and treating diabetes and diabetes-related complications, and/or reversing diabetes in a subject in need thereof, wherein the Pdia4 inhibitor inhibits Pdia4 protein activity and/or inhibits Pdia4 protein expression.

Alternatively, the invention relates to a method for preventing, alleviating and treating diabetes and/or diabetes-related complications, and/or reversing diabetes in a subject in need thereof, comprising: administering to the subject a therapeutically effect amount of a Pdia4 inhibitor and one other anti-diabetic agent in combination therapy to alleviate, treat diabetes and diabetes-related complications, and/or reverse diabetes in the subject, wherein the Pdia4 inhibitor inhibits Pdia4 protein activity and/or inhibits Pdia4 protein expression.

In another aspect, the invention relates to a method of diagnosing, treating and monitoring diabetes, which comprises;
(a) quantifying blood Pdia4 protein level in a subject;
(b) identifying the subject as a diabetic when the blood Pdia4 protein level is higher than a normal control subject;
(c) subjecting the subject identified as the diabetic to an anti-diabetic agent;
(d) further quantifying the blood Pdia4 protein level in the subject identified as the diabetic after being subjected to the anti-diabetic agent; and
(e) determining that the subject after being subjected to the anti-diabetic agent shows an improvement of the diabetes when there is a decrease in the blood Pdia4 protein level as compared to before being subjected to the anti-diabetic agent.

In one embodiment of the invention, the anti-diabetic agent comprises a Pdia4 inhibitor.

Further in another aspect, the invention relates to a method of screening for a Pdia4 inhibitor and/or an anti-diabetic agent, which comprises;
(a) quantifying blood Pdia4 protein level in a diabetic animal before and after administering to the diabetic animal a test compound; and
(b) identifying the test compound as the Pdia4 inhibitor and/or the anti-diabetic agent when there is a decrease in the blood Pdia4 protein level in the diabetic animal after being administered the test compound; or
(i) measuring activity of Pdia4 protein in the presence and absence of a test compound; and
(ii) identifying the test compound as the Pdia4 inhibitor and/or the anti-diabetic agent when there is a decrease in the activity of the Pdia4 protein in the presence of the test compound,
wherein the Pdia4 inhibitor inhibits Pdia4 protein activity or inhibits Pdia4 protein expression.

Further in another aspect, the invention relates to a method of screening for a Pdia4 inhibitor, comprising:
(i) incubating reduced BPTI with GST-Pdia4 in the presence and absence of a test compound identified in a buffer solution;
(ii) measuring the amount of the reduced PBTI in the presence and absence of the test compound identified in step (c) in the buffer solution; and
(iii) identifying the test compound as a Pida4 inhibitor.

Yet in another aspect, the invention relates to a method of treating pre-diabetes or diabetes in a subject, comprising: (a) administering to the subject a therapeutically effective amount of a Pdia4 inhibitor; (b) identifying the pre-diabetes or diabetes in the subject as Pdia4 inhibition-responsive by monitoring the level of blood glucose or insulin, and/or pancreatic β-cell function and mass over a period of time after said administration to the subject, wherein an improvement in the level of blood glucose or insulin, and/or maintenance of pancreatic β-cell function and/or mass identifies the pre-diabetes or diabetes in the subject as Pdia4 inhibition-responsive; and (c) further administering the Pdia4 inhibitor or a different Pdia4 inhibitor to the subject.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIGS. 2A-D show that the level of Pdia4 protein in β cells is up-regulated in response to metabolic stress. (A-C) Min-6 cells, a β cell line, were treated with the indicated concentrations of glucose (A), palmitate (B) and STZ (C) for 48 hr. Total lysate was subjected to SDS-PAGE and Western blotting with antibodies against Pdia4 or Actin. (D) Pancreatic islets of diabetes-free wild-type (WT) and diabetic $lepr^{db/db}$ mice were isolated and lyzed, followed by Western blotting with anti-Pdia4 and anti-Actin antibodies. Results are expressed as mean±SEM from 3 independent experiments. *P<0.05; P<0.01; *P<0.001.

FIGS. 6A-E show that Pdia4 deficiency reduces diabetes-related complications in a mouse model of diabetes. (A) Six-week-old wild-type (WT) and $pdia4^{-/-}$ mice received an i.p. injection of PBS or STZ (80 mg/kg BW/day) for 3 consecutive days. Four weeks later, the mice receive a whole body X-ray analysis. Bone density of the mice was shown and arrows indicate femurs and knee joints. (B-C) Six-week-old wild-type (WT) and $pdia4^{-/-}$ mice were wounded on skin (B) and cornea (C) using skin puncher and sodium hydroxide, respectively. Images of the wounds at the indicated time points were shown. (D). Urine samples of $lepr^{db/db}$ and $pdia4^{-/-}lepr^{db/db}$ mice at the age of 30 weeks were collected and measured. The creatinine clearance ratio (CCR) are shown. (E). Blood samples of $lepr^{db/db}$ and $pdia4^{-/-}lepr^{db/db}$ mice at the age of 46 weeks were collected and measured. The level of triglyceride and high density lipoprotein (HDL) is shown.

FIGS. 8A-C illustrate chemical structures of some of the identified Pdia4 inhibitors (A), their bioactivities (B) and relative inhibition (%) (C), respectively. Pdia4 (abbreviated as A4) was incubated with its substrate, insulin, in the absence and presence of Pdia4 inhibitors (109291, 156588, 156590, 302308 and CP).

DETAILED DESCRIPTION OF THE INVENTION

Definitions

Figure 1A:
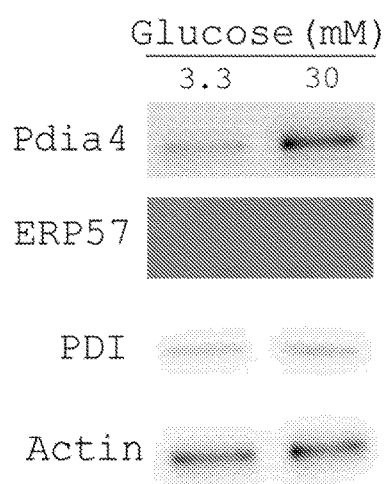
FIGS. 1A-C show the level of Pdia4 protein in β cells, blood and other tissues. (A) Mouse islets were treated with the indicated concentrations of glucose for 48 hr. Total lysate was subjected to SDS-PAGE and Western blotting with the indicated antibodies (B) Serum Pdia4 protein levels of non-diabetic (WT) and diabetic db/db mice were respectively quantified using an ELISA kit with anti-Pdia4 antibody. (C) Different mouse tissues were collected and analyzed for Pdia4 protein level, Western blotting was performed as FIG. 1B. Results are expressed as mean±SEM from 3 independent experiments. *P<0.05; P<0.01; *P<0.001.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "treating" or "treatment" refers to administration of an effective amount of a therapeutic agent to a subject in need thereof with the purpose of cure, alleviate, relieve, remedy, ameliorate, or prevent the disease, the symptoms of it, or the predisposition towards it. Such a subject can be identified by a health care professional based on results from any suitable diagnostic method.

"An effective amount" refers to the amount of an active agent that is required to confer a therapeutic effect on the treated subject. Effective doses will vary, as recognized by those skilled in the art, depending on routes of administration, excipient usage, and the possibility of co-usage with other therapeutic treatment.

Pdia4 refers to protein disulfide isomerase family A, member 4. The sequence of human Pdia4 protein is shown in SEQ ID NO: 5. Examples of the sequences of shRNAs are shown in SEQ ID NOs: 1-4.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses "a human equivalent dose" may be obtained by calculations from the following formula:

HED=animal dose in mg/kg×(animal weight in kg/human weight in kg)$^{0.33}$.

Nothing is known about the role of Pdia4 in diabetes. The invention relates to the discovery of the expression of Pdia4 in response to metabolic stress. The invention also relates to the discovery of Pdia4 role in β-cell function and mass. The invention further relates to the discovery of the impact of a combination of Pdia4 deficiency/inhibition and insulin sensitizers on T2D development. The invention also relates to the discovery of the role of Pdia4 in T2D complications. Pdia4 expression was up-regulated in response to metabolic stress such as glucose, lipid and chemicals at high dose. Blood Pdia4 was increased in diabetic mice as opposed to diabetes-free mice. This enables Pdia4 as a good indicator for diagnosis of diabetes. Consistently, Pdia4 ablation reduced diabetic complications such as osteoporosis, skin ulcer, eye disease, renal diseases and cardiovascular diseases. Besides, Pdia4 can be used to screen and identify Pdia4 inhibitors as anti-diabetic agents.

The unique features of the Invention and advantages when compared to the existing technologies are as follows: (1) No report has shown a link between diabetes and Pdia4; (2) It was discovered that the expression levels of Pdia4 are up-regulated in β cells and blood of diabetic mice; (2) It was also discovered that Pdia4 is localized in nuclear, cytosolic and membrane compartments. The commercial applications of the Invention include, but not limited to, use of Pdia4 as diagnosis marker for diabetes, use of Pdia4 as the target of anti-diabetic therapy and use of targeting Pdia4 alone and in combination with other anti-diabetic drugs to prevent and cure diabetes

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Research Design and Methods

Reagents, Cells and Animals

Streptozotocin (STZ), glucose, palmitate, Dihydroethidium (DHE), metformin, and rosiglitazone were purchased from Sigma-Aldrich. Hematoxylin was purchased from Biocare Medical Inc. Eosin was purchased from Muto Pure Chem Inc. MIN6 cells, a mouse β-cell line, were cultured in RPMI-1640 (Invitrogen) containing 20% PBS and 5% penicillin/streptomycin. The cells were grown at 37° C. in a humidified atmosphere with 5% $CO_2$. C57BL/6 and lepr$^{db/m}$ mice were purchased from Jackson laboratory. To generate pdia4$^{-/-}$ C57BL/6 mice, Pdia4 gene targeting vector was first constructed using a bacterial artificial chromosome (BAC) recombineering strategy. Briefly, a 230-kb BAC clone (Geneservice, USA) contains an entire allele of mouse pdia4 gene as indicated. The Neo cassette, composed of two homology arms, two loxP sites, and a Neo gene, was inserted into the intron 6 of pdia4 gene in the BAC via homologous recombination. After the first Neo cassette was popped out by Cre, the second Neo cassette, containing two homology arms, two frt sites, one loxP site and a Neo gene was inserted into the intron 2 of pdia4 gene in the BAC via homologous recombination. Following linearization, this BAC construct was electroporated into C57BL/6 ES cells. After recombination screening, the targeted ES lines were selected for blastocyst injection and, in turn, generation of chimeric mice. To generate pdia4$^{-/-}$ mice, the chimeric mice were first bred with C57BL/6 mice to obtain pdia4$^{floxed/+}$ mice, followed by a sibling breeding. Subsequently, pdia4$^{floxed/floxed}$ mice were crossed with EIIa/Cre deleter mice to obtain the pdia4$^{+/-}$ mice whose exons 3 to 6 were deleted. Sibling mating of mice produced wild-type (pdia4$^{+/+}$), pdia4$^{+/-}$ and pdia4$^{-/-}$ mice, followed by the genotyping analysis with PCR and Western blot. Besides, pdia4$^{-/-}$ mice were bred with lepr$^{db/m}$ mice to obtain pdia4$^{-/-}$lepr$^{db/db}$ mice. All animals had free access to chow and water, and were maintained at 21-23° C. with 12 hr light-12 hr dark cycles in the institutional animal facility. All mouse work was handled according to the guidelines of the Academia Sinica Institutional Animal Care and Utilization Committee.

Drug Administration and Measurement of Metabolic Parameters

To deplete pancreatic β cells in mice. 6-week-old WT and pdia4$^{-/-}$ C57BL/6 mice were intraperitoneally injected with STZ at 80 mg/kg for 3 consecutive days. Additionally, some WT and pdia4$^{-/-}$ mice were received saline as vehicle control. To determine the levels of fasting blood glucose, the mice were fasted for overnight alter the final STZ administration. Next day, the mice had free access to feed for 2 hr, followed feed removal. After 0.5 hr, the levels of postprandial blood glucose and insulin were determined. Blood glucose level was monitored on day 0, 3, 5, 7, 9, 11 and 13 after the final injection of STZ. Diabetic hyperglycemia was defined as a fasting blood glucose concentration≥200 mg/dl for two or more consecutive tests. To treat mice, PBS or a combination of cytopiloyne (2.5 mg/kg/day), metformin (60 mg/kg/day), and metformin (60 mg/kg/day) plus rosiglitazone (20 mg/kg/day) were fed for the indicated time. Postprandial blood glucose was measured. To treat pdia4$^{-/-}$lepr$^{db/db}$ mice, PBS, metformin (60 mg/kg/day), and metformin (60 mg/kg/day) plus rosiglitazone (20 mg/kg/day) were fed for the indicated time. Postprandial blood glucose was measured.

Apoptosis Assays

Terminal deoxynucleotidyl transferase dUTP nick end labeling (TUNEL) assays were performed using the ApopTag In Situ Apoptosis Detection Kit (Millipore). The TUNEL-positive cells were photographed with Axio Vision microscopy (Carl Zeiss) and counted manually from the images. The islets area was measured using Axio Vision program (Carl Zeiss).

Measurement of Glucose and Insulin.

After the overnight fasting, the mice had free access to food for 2 hr. fasting or postprandial blood glucose levels of the mice were measured using an Elite glucometer (Bayer). Insulin levels in blood samples or mouse islet supernatants were determined by ELBA assays (Mercodia).

Measurement ROS Production

Dihydroethidium (DHE) is reactive with superoxide anion and forms a red fluorescent product—ethidium, which intercalates with DNA. Pancreatic frozen sections or mouse islets were incubated with 10 nM DHE at 37° C. for 10 min. After washing with ddH$_2$O for three times, ethidium staining was visualized with Axio Vision fluorescent microscopy (Carl Zeiss). The fluorescence intensity of pancreatic islet cells was quantified using Axio Vision program (Carl Zeiss).

Pancreatic Islet Isolation and Measurement of Insulin Secretion

Eighteen-week-old mice were fasted overnight. Their pancreata were digested with collagenase P (Roche) digestion and harvested with histopaque-1077 (Sigma) gradient centrifugation. The pancreatic islets (5 islets/well) were incubated with Krebs-Ringer bicarbonate (KRB) buffer in the presence of basal glucose (3.3 mM) or high glucose (16.7 mM) for 30 min. The supernatants were collected for insulin ELBA assays.

Western Blot Analysis

MIN6 cells or mouse islets were starved in RPMI glucose-free medium for 1 hr. The cells or islets were then treated with indicated glucose concentrations for 48 hr. For high fat treatment, the cells or islets were then treated with vehicle or 0.4 mM palmitate (containing 5.6 mM glucose and 0.92% BSA) for 48 hr. For STZ treatment, the cells or islets were then treated with vehicle or 10 mM STZ for the indicated time. After extensive washing, the cells or mouse islets were lysed with lysis buffer (10 mM Tris-HCl pH 7.4, 10 mM KCl, 1.5 mM MgCl$_2$, 250 mM sucrose, 1 mM EDTA, 1 mM EGTA, 1% NP-40 and 1× protease inhibitor). After centrifugation, total lysates underwent SDS-PAGE and protein transfer to PVDF membrane. After blocking, the membrane was probed with the indicated antibodies.

Bovine Pancreatic Trypsin Inhibitor (BPTI)-Based Assay

Glutathione agarose bead-bound GST-Pdia4 (0.15 µg) were purified from E. coli bacteria. To test effect of CP on disulfide isomerase activity of GST-Pdia4, reduced BPTI (0.39 µg) was incubated with redox buffer in the presence of vehicle, 5.64 µg GST-Pdia4 or 5.64 µg GST-Pdia4 plus different doses of CP (0, 0.33 µg, 3.3 µg and 33 µg. Enzymatic activity of GST-Pdia4, shown as the percentage of reduced BPTI (%) as described.

Evaluation of Diabetic Complications

To assess the bone density, wild-type mice and pdia4$^{-/-}$ mice, which were treated with PBS or STZ, received a whole-body X-ray analyses. Bone density and medullary cavity of femurs and knee joints are indicated. To evaluate skin ulcer, the wild-type mice and pdia4$^{-/-}$ mice, which were treated with PBS or STZ, were injured by punchers. The wound was measured using caliper. For eye injury, the wild-type mice and pdia4$^{-/-}$ mice, which were treated with PBS or STZ, were injured by sodium hydroxide. Eye damage was photographed when the mice were exposed to UV light. To evaluate renal function in diabetic mice, urine samples of the lepr$^{db/db}$ and pdia4$^{-/-}$lepr$^{db/db}$ mice at 18 weeks were collected and analyzed for creatinine using creatinine assay kits (ab65340). Biochemical parameters of the blood samples was determined using 7600 Clinical Anazyler (Hitachi).

Pdia4 Assay

Insulin (200 µM) was incubated with recombinant Pdia4 (1.65 µg) in the presence of vehicle or CP at the indicated, doses for 30 min at 25° C. in redox buffer. Inhibition of the enzymatic activity of Pdia4 was obtained by the formula, 100%×(OD$_{595}$ of vehicle−OD$_{595}$ of CP)/(OD$_{595}$ of vehicle).

Virtual Screening

To prepare chemical database, an n-house chemical library (261 compounds) were converted to 3D coordinates using forced field CHARMrn to minimize compounds by Discovery Studio/Prepare Ligand Module. To prepare protein structure, the crystal structure of the Pdia4 active domain from PDB was used. The protonation states of residues were adjusted to the dominant ionic forms at pH 7.5. Molecular docking was performed with GOLD version 5.1 (CCDC Software Limited, Cambridge, I.T.K.). GOLD was used to dock in-house chemical library onto active domain of Pdia4 protein with flexible docking option turned on. During the following docking procedure, the side chain structure of the Cys260 and Cys269 amino acid residues remained flexible, modeled with the built-in rotamer libraries of the GOLD package. Initial 100 independent genetic algorithm cycles of computation were carried out with ligand torsion angles varying between −180 and 180 degree. The search efficiency was set at 100% to ensure the most exhaustive search for the docking conformational space. For effective usage of computational resources, the docking-calculation was confined in an active site-centered 15 Å radius sphere, which enclosed all possible compounds under the applied constraints. All default parameters were used for the GOLD genetic algorithm. The resultant ligand-protein complex structures were ranked with the GOLDSCORE scoring function to determine the top hits (8,14-dihydroxy-12-O-(4,5-dimethylhexanoyl)-17-methyl-3-orthenthosyl-pregnenolone, 12-O-acetyl-8,14-dihydroxy-17-methyl-3-orthenthosyletienic acid and 12-O-cinnamoyl-8,14-dihydroxy-17-methyl-3-orthenthosyletienic acid). The same strategy for CP and its derivatives were performed.

Results

Pdia4 Protein is Upregulated in Response to Metabolic Stress in β Cells in the Blood of Diabetic Mice.

Figure 1B:
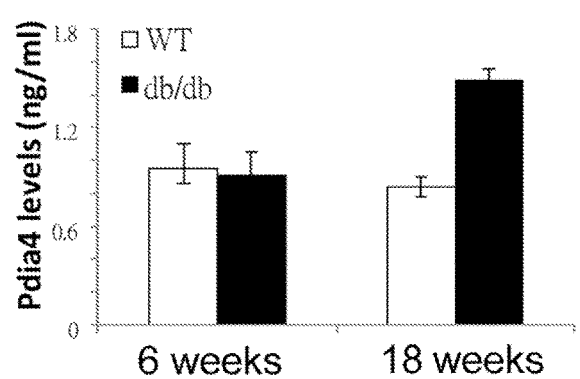
Figure 1C:
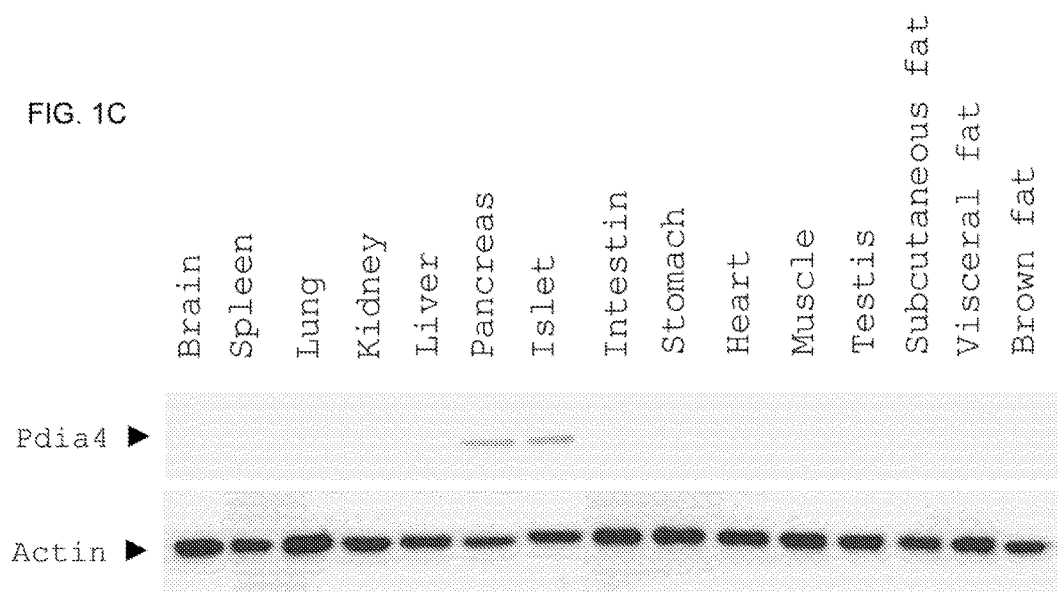

To explore the role of Pdia4 in β cells and diabetes, we first assessed the expression of Pdia4 in mouse islets. We found that Pdia4 was primarily expressed in pancreata, pancreatic islets and liver (FIGS. 1A-C). More importantly, the protein level of Pdia4, but not PDI and ERP57, in pancreatic islets was up-regulated in response to high glucose (FIG. 1A). We also confirmed that the level of Pdia4 in β cells was up-regulated in response to metabolic stress (FIGS. 2A-C). Similarly, Pdia4 protein level in the β cells of diabetic $lepr^{db/db}$ mice was increased (FIG. 2D).

To test the correlation between Pdia4 protein level and diabetes, we measured the protein level of blood Pdia4 in diabetes-free and diabetic C57BL/6 and $lepr^{db/db}$ mice using Elisa kits. Our results showed that the level of blood Pdia4 protein was constantly low in diabetes-free C57BL/6 mice aged 6 or 18 weeks and $lepr^{db/db}$ mice aged 6 weeks (FIG. 1B). However, the Pdia4 concentration was significantly up-regulated in the blood of diabetic 18-week-old mice (FIG. 1B). The data suggest that blood Pdia4 is a diagnosis marker of diabetes.

Pdia4 Deficiency Increases Insulin Secretion and Islet Preservation but Decreases ROS in β Cells.

Figure 3A:
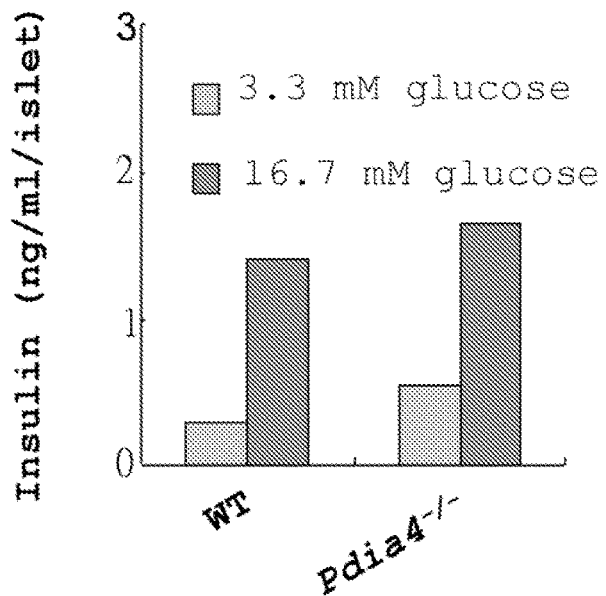
FIGS. 3A-C show that Pdia4 deficiency increases β-cell function and islet protection. (A). Mouse islets of wild-type (WT) and $pdia4^{-/-}$ mice were stimulated with the indicated doses of glucose (3.3 mM versus 16.7 mM) for 30 min. The level of insulin in the supernatants was determined. (B) Wild-type (WT) and $pdia4^{-/-}$ mice received a single intraperitoneal (i.p.) injection of STZ at 80 mg/kg body weight (BW). After sacrifice, the level of reactive oxygen species (ROS) in the mouse islets was determined using relative dihydroethidium fluorescence and islet size. (C) Wild-type (WT) and $pdia4^{-/-}$ mice received 3 doses of STZ at 80 mg/kg body weight (BW). The pancreata were removed from the mice and stained with anti-insulin antibody as well as hematoxylin and eosin (H&E). The islet area was determined based on the islet morphology shown by histochemical staining. The data are expressed as mean±SEM. *P<0.05; **P<0.01.
Figure 3B:
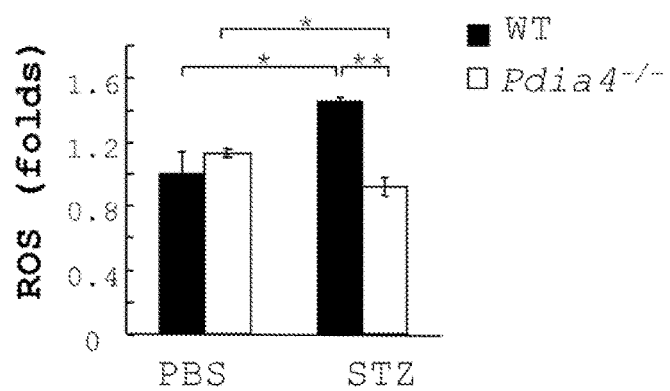
Figure 3C:
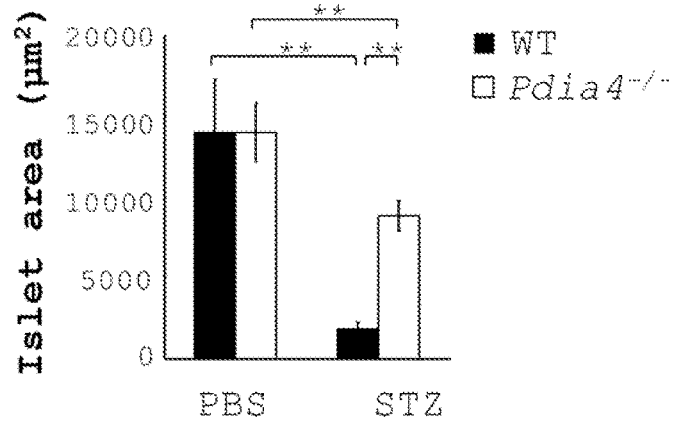

Next, we investigated the gene function of Pdia4 in β-cell function and preservation. We compared the insulin secretion from mouse islets of wild-type and $pdia4^{-/-}$ mice. The $pdia4^{-/-}$ islets released insulin 2-fold more than wild-type islets in the presence of 3.3 mM glucose (FIG. 3A). The $pdia4^{-/-}$ islets released insulin to a greater extent than wild-type islets in the presence of 16.7 mM glucose (FIG. 3A). The data suggest that Pdia4 deficiency enhances β-cell function. We also measured ROS level in mouse islets in wild-type and $pdia4^{-/-}$ mice treated with one dose of PBS or STZ. We found that STZ significantly augmented the ROS level in the islets of wild-type mice (FIG. 3B). In contrast, $pdia4^{-/-}$ islets produced lower ROS level than wild-type islets (FIG. 3B). The data suggest that Pdia4$^{-/-}$ deficiency reduces ROS accumulation. Besides, we evaluated islet architecture in wild-type and $pdia4^{-/-}$ mice treated with 3 doses of PBS or STZ. We found that $pdia4^{-/-}$ islets were more resistant to STZ-mediated apoptosis than wild-type islets as evidenced by islet area (FIG. 3C).

Pdia4 Deficiency Lowered Blood Glucose in Mouse Models of Diabetes Through Enhanced β-Cell Function and Reduced Islet Cell Death.

Figure 4A:
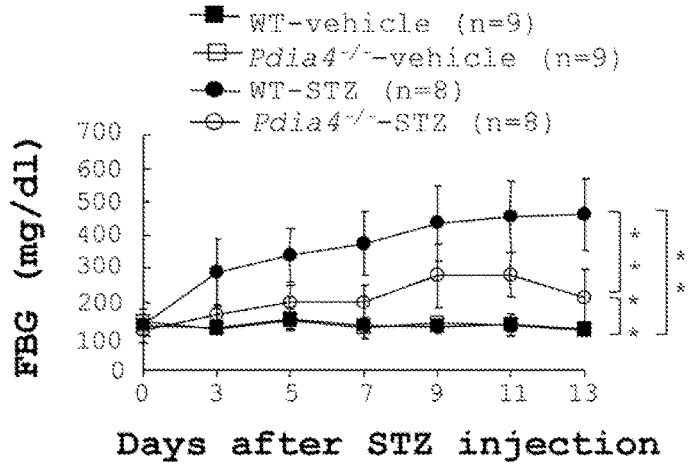
FIGS. 4A-F show that Pdia4 deficiency inhibits diabetes development in chemical-induced and spontaneous models of diabetes. (A-B) Fasting blood glucose (FBG, panel A) and postprandial blood glucose (PPBG, panel B) of the same mice from FIG. 3C were measured using a glucometer at the indicated ages. (C-D) Wild-type (WT), $pdia4^{-/-}$, $lepr^{db/db}$ and $pdia4^{-/-}lepr^{db/db}$ mice were fed with a standard diet. Their fasting blood glucose (FBG, panel C) and postprandial blood glucose (PPBG, panel D) of the mice were measured using a glucometer at the indicated ages. (E-F) The HOMA-β (E) of the mice from FIG. 4C was obtained based on the formula HOMA-β=20×insulin (μU/mL)/(glucose (mmol/L)−3.5). (F) The number of the dead cells of the same mice from FIG. 4C was quantified using TUNEL assays. The number of mice (n) is indicated in parentheses. *P<0.05 vs WT; #P<0.05 vs $lepr^{db/db}$.
Figure 4B:
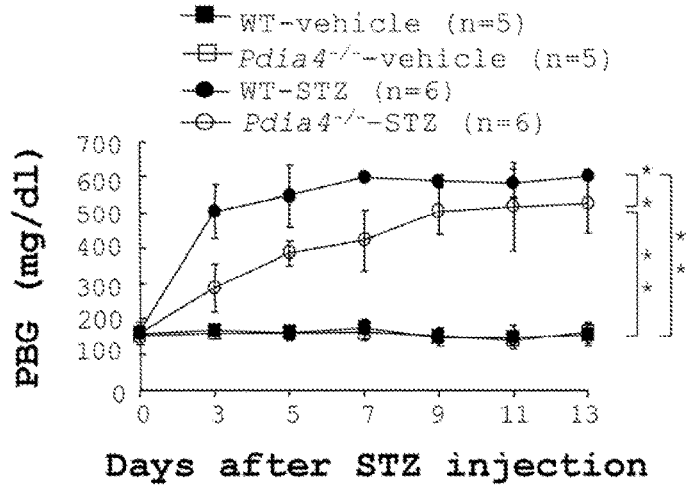
Figure 4C:
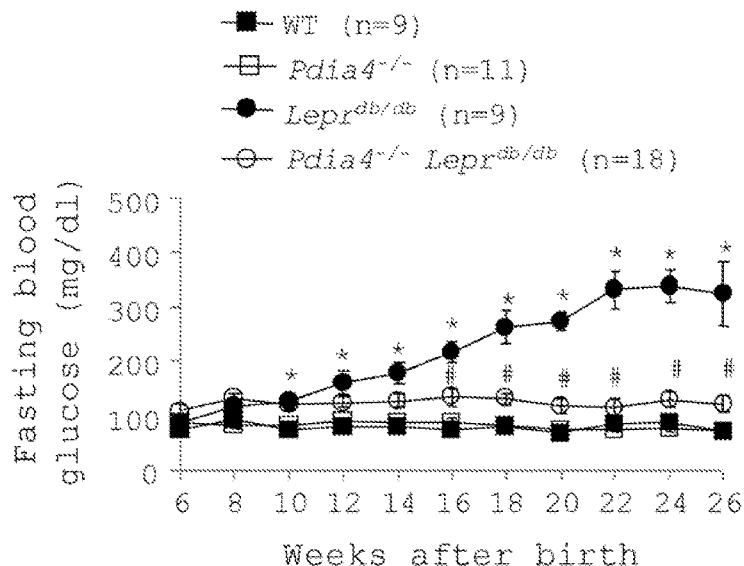
Figure 4D:
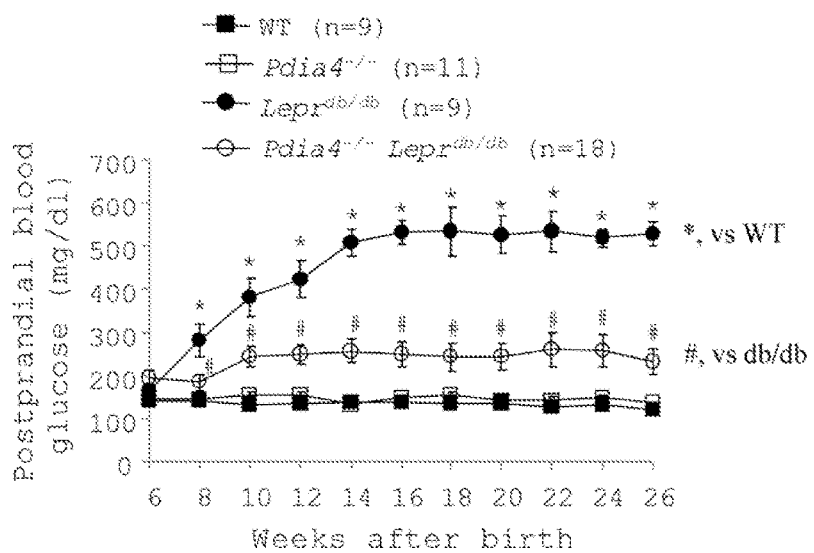

To evaluate the gene function of Pdia4 in diabetes development, we first used the chemical STZ to induce diabetes in wild-type and $pdia4^{-/-}$ mice. We found that wild-type mice had similar fasting blood glucose and postprandial blood glucose as $pdia4^{-/-}$ mice (FIGS. 4A-B). In contrast, STZ-treated wild-type mice had higher fasting blood glucose and postprandial blood glucose than STZ-treated $pdia4^{-/-}$ mice (FIGS. 4A-B). Consistent with the data obtained from FIG. 3C, the data obtained from FIGS. 4A-B suggest that Pdia4 deficiency confers protection against β cells and diabetes in mouse islets. We also compared diabetes development in $lepr^{db/db}$ and $pdia4^{-/-}lepr^{db/db}$ mice. The $lepr^{db/db}$ mice spontaneously developed diabetes from the age of 8 weeks and beyond as shown by fasting blood glucose (FIG. 4C) and postprandial blood glucose (FIG. 4D). In contrast, the $pdia4^{-/-}lepr^{db/db}$ mice had lower lasting blood glucose (FIG. 4C) and postprandial blood glucose (FIG. 4D) than $lepr^{db/db}$ mice. The data suggest that Pdia4 deficiency confers protection against β cells and diabetes in mouse islets (FIGS. 4C-D).

Figure 4E:
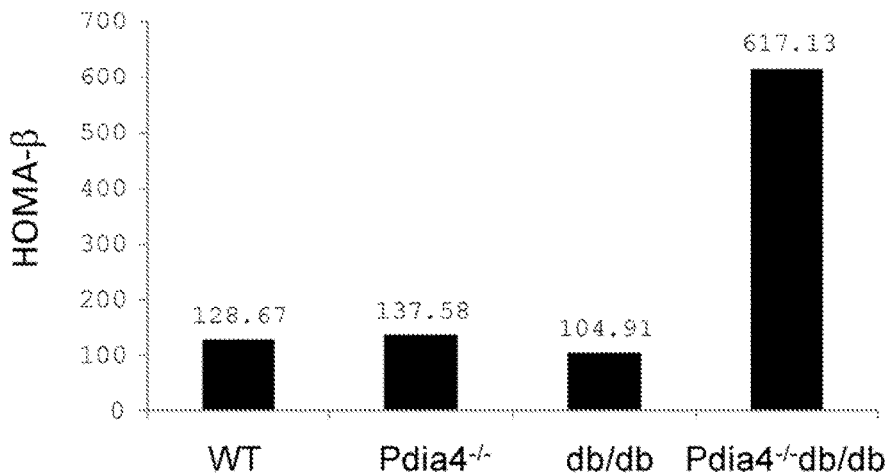

Homeostatic model assessment (HOMA) is used to assess β-cell function. Wild-type mice had slight lower HOMA-β values than $pdia4^{-/-}$ mice (FIG. 4E). In contrast, $pdia^{-/-}lepr^{db/db}$ mice had dramatically higher HOMA-β values than $lepr^{db/db}$ mice (FIG. 4E). The data imply that Pdia4 deficiency improves β-cell function.

Figure 4F:
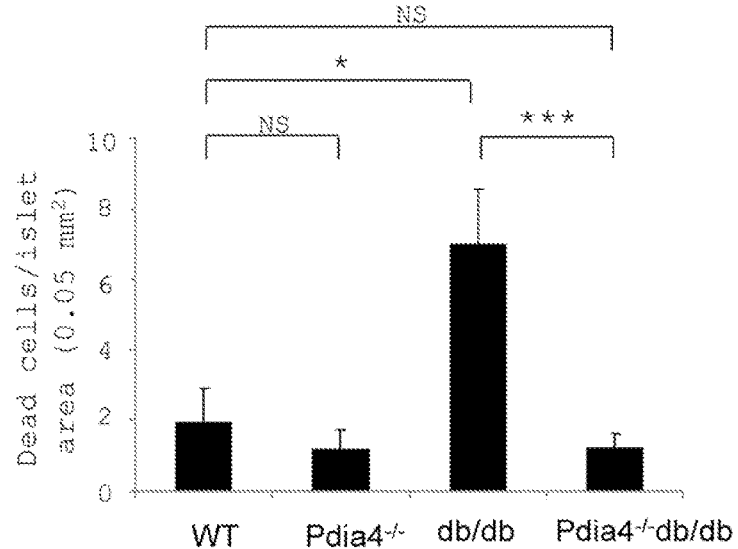

Next, we studied the impact of Pdia4 on death in wild-type C57BL/6, $pdia4^{-/-}$ C57BL/6, $lepr^{db/db}$ and $pdia4^{-/-}lepr^{db/db}$ mice. We found that $pdia4^{-/-}$ mice had slightly lower cell death of pancreatic islets than wild-type mice. Accordingly, $pdia4^{-/-}lepr^{db/db}$ mice had much lower cell death of pancreatic islets than $lepr^{db/db}$ mice (FIG. 4F).

Overall, the data showed that Pdia4 deficiency reduced diabetes via the improvement of β-cell function and survival.

A Combination of Pdia4 Deficiency/Inhibition and Lowered Insulin Resistance can Reverse Diabetes.

Figure 5A:
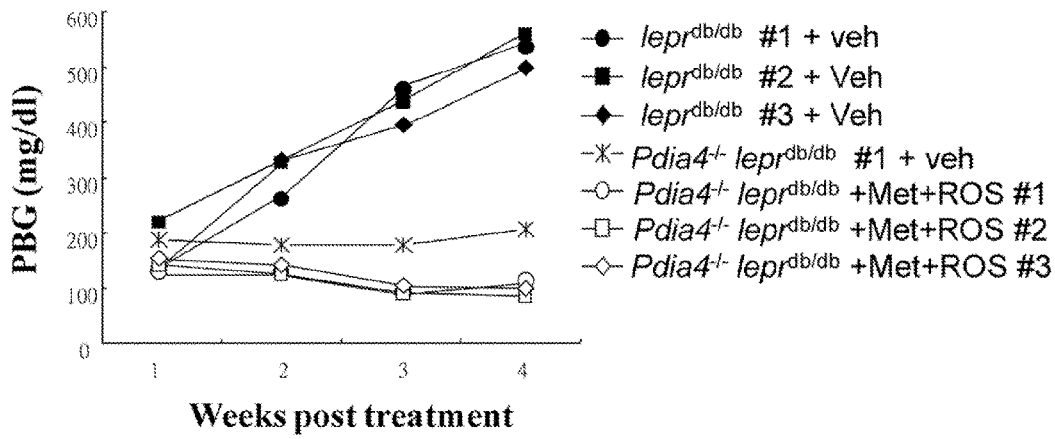
FIGS. 5A-C show that a combination of Pdia4 deficiency/inhibition and insulin sensitizers can reverse diabetes. (A) $lepr^{db/db}$ and $pdia4^{-/-}lepr^{db/db}$ mice received a daily dose of PBS vehicle (Veh), metformin (MET, 60 mg/kg BW) and metformin (MET, 60 mg/kg BW)/rosiglitazone (ROS, 20 mg/kg BW). Their postprandial blood glucose was determined using a glucometer. (B) Inhibition of the disulfide isomerase activity of GST-Pdia4 by cytopiloyne. Reduced BPTI was incubated with redox buffer in the presence of vehicle. GST-Pdia4 or GST-Pdia4 with CP at different doses. Enzymatic activity of GST-Pdia4 was presented as the percentage of the decrease in the reduced BPTI. (C) $lepr^{db/db}$ mice received a daily dose of PBS vehicle (Veh), cytopiloyne (CP, 2.5 mg/kg), cytopiloyne (CP, 2.5 mg/kg)/metformin (MET, 60 mg/kg BW) and cytopiloyne (CP, 2.5 mg/kg)/metformin (MET, 60 mg/kg BW)/rosiglitazone (Ros, 20 mg/kg BW). Their postprandial blood glucose was determined using a glucometer.

Preserving β cells hold the key to curing diabetes. Our data showed that Pdia4 deficiency improved β-cell function and preservation but failed to reverse diabetes. Next, we investigated the combination effect of Pdia4 ablation/inhibition and insulin sensitizer, metformin (60 mg/kg BW), rosiglitazone (20 mg/kg BW) or both, on diabetes in $pdia4^{-/-}lepr^{db/db}$ and $lepr^{db/db}$ mice. We indicated that $lepr^{db/db}$ mice had higher postprandial blood glucose (FIG. 5A). In contrast, $pdia4^{-/-}lepr^{db/db}$ mice had the postprandial blood glucose of 200 mg/dL (FIG. 5A). Treatment with metformin (60 mg/kg BW), rosiglitazone (20 mg/kg BW) or both, could normalize hyperglycemia in $pdia4^{-/-}lepr^{db/db}$ mice (FIG. 5A). The data showed that Pdia4 deficiency and insulin sensitizer(s) could cure diabetes.

Figure 5B:
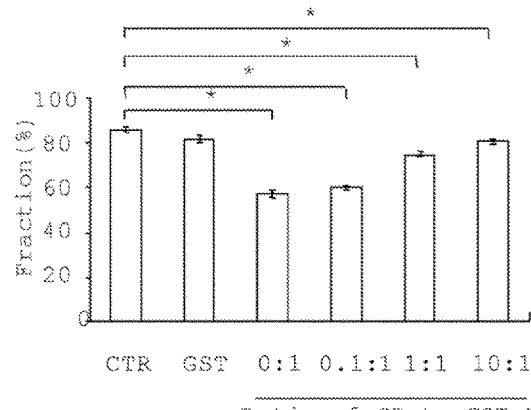
Figure 5C:
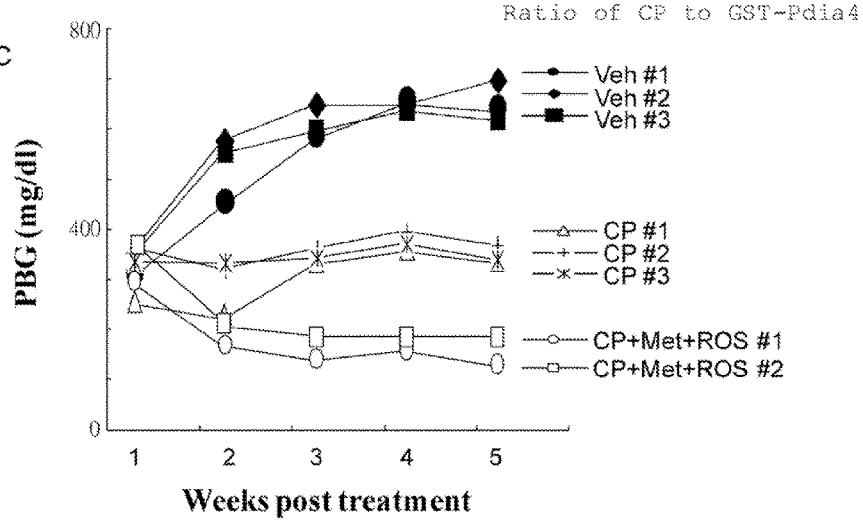
Figure 7A:
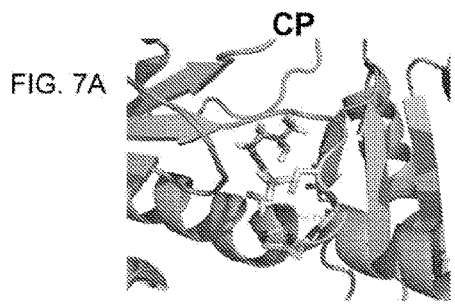
FIGS. 7A-E show screening and identification of Pdia4 inhibitors using virtual screening and chemical structures of the Pdia4 inhibitors. The active domain of Pdia4 was used to screen Pdia4 inhibitors. (A) Structure of the active domain of Pdia4 in complex with CP. (B-D) Structure of the active domain of Pdia4 in complex with compounds 00322271 (B), 00547011 (C) and 00244418 (D). Active domain of Pdia4 and compounds are indicated in green and brown, respectively. (E) Structure of the terpenes with the best fit for the Pdia4 active domain.
Figure 7B:
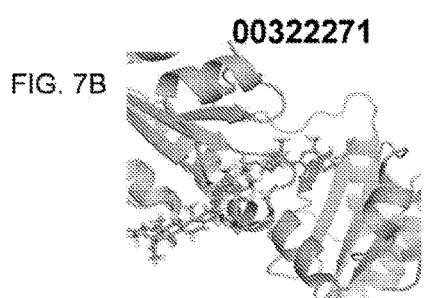
Figure 7C:
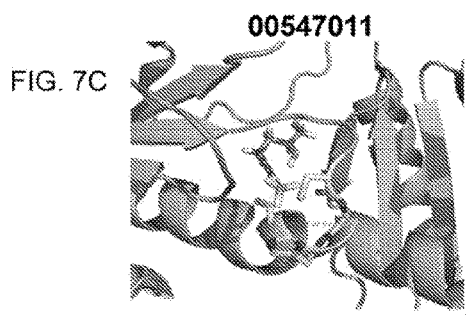
Figure 7D:
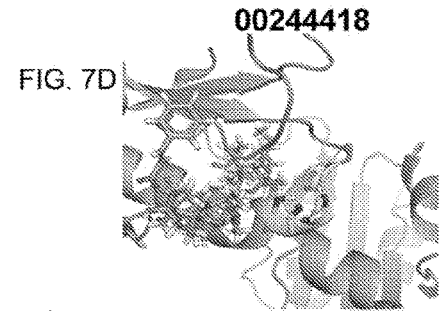
Figure 7E:
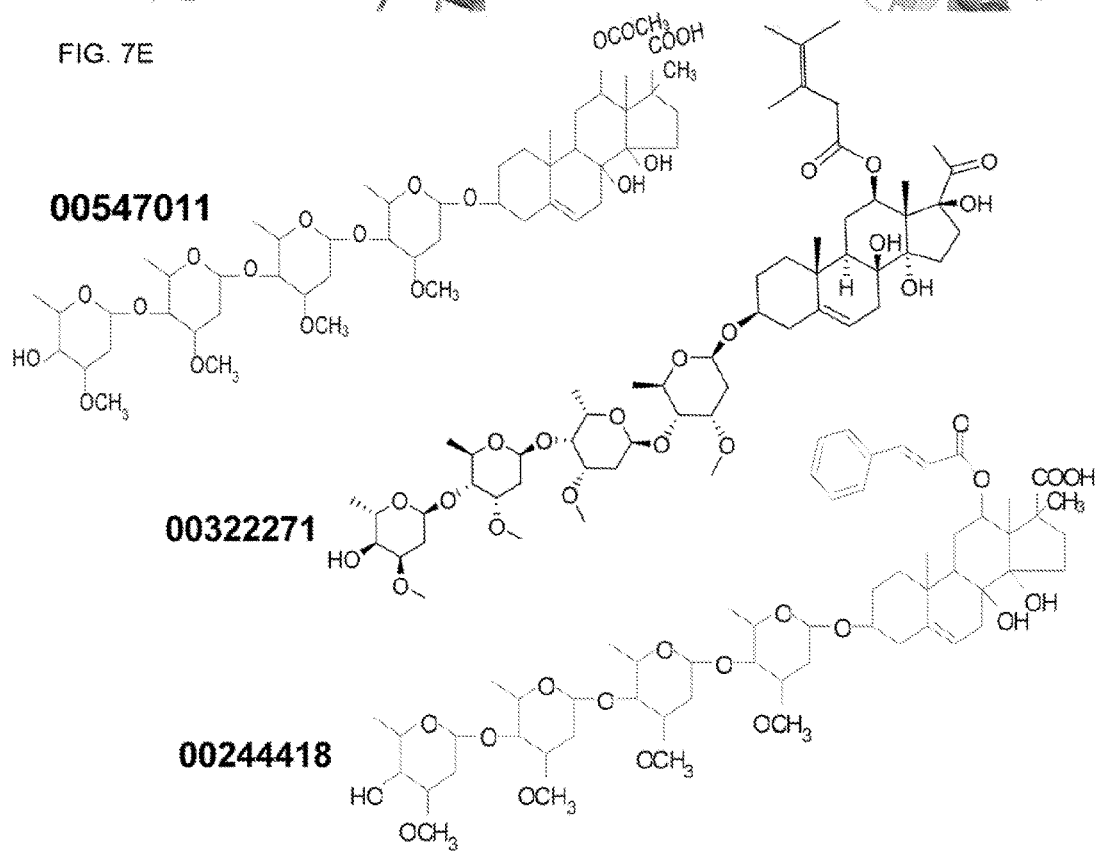

Cytopiloyne was shown to suppress the enzymatic activity of Pdia4 (FIG. 5B). We also examined the effect of a combination of cytopiloyne and insulin sensitizer(s) (metformin, rosiglitazone or both) on diabetes in $lepr^{db/db}$ mice. The $lepr^{db/db}$ mice had higher postprandial blood glucose (FIG. 5C). In contrast, cytopiloyne could lower postprandial blood glucose in $lepr^{db/db}$ mice (FIG. 5C). Moreover, a combination of cytopiloyne and metformin or metformin plus rosiglitazone completely normalized the postprandial blood glucose in $lepr^{db/db}$ mice (FIG. 5C). The data exhibited that Pdia4 inhibition and insulin sensitizer(s) could cure diabetes.

Overall, the data suggest that Pdia4 depletion/inhibition together with sensitizer(s) can reverse diabetes.

Effect of Pdia4 on Diabetes-Related Complications

We also investigated the gene function of Pdia4 in diabetes-related complications such as nephropathy, osteoporosis, skin ulcer and eye damage. We compared osteoporosis of femur and knee joints in diabetic wild-type C57BL/6 and $pdia4^{+/-}$ C57BL/6 mice following STZ treatment. The data from whole-body X-ray analysis showed that bone density in wild-type and $pdia4^{-/-}$ mice was reduced 4 weeks post STZ treatment (FIG. 6A). Interestingly, the medullary cavity in $pdia4^{-/-}$ mice was bigger than in wild-type mice (FIG. 6A). However, $pdia4^{-/-}$ mice had denser femur head than wild-type mice 4 weeks post STZ treatment (FIG. 6A). The data indicated that Pdia4 deficiency reduced osteoporosis.

Next, we evaluated the impact of Pdia4 on wound healing in wild-type and $pdia4^{-/-}$ mice. We found that $pdia4^{-/-}$ mice had better wound healing than wild-type mice (FIG. 6B).

Similarly, pdia4$^{-/-}$ mice recovered from corneal injury than wild-type mice (FIG. 6C). Besides, we also found that pdia4$^{-/-}$lepr$^{db/db}$ mice had higher creatinine clearance rate than lepr$^{db/db}$ mice (FIG. 6D), suggesting that Pdia4 deficiency reduces nephropathy. Finally, we examined the impact of Pdia4 in cardiovascular disease (CVD). We found that Pdia4 deficiency reduced serum triglyceride and increased high density lipoprotein (HDL) (FIG. 6E), suggesting that Pdia4 deficiency rescues CVD.

The overall data suggest that Pdia4 negatively regulates diabetes-related complications. Taken together, Pdia4 serves as a diagnosis marker and therapeutic target of diabetes and its complications.

Pdia4 Can be Used to Screen Pdia4 Inhibitors for Diabetes

Using a virtual screening strategy to assess an in-house library containing 261 compounds, we found that cytopiloyne, cytopiloyne derivatives, and 3 other terpenoids have the best fit for Pdia4 active sites (FIG. 7). We also confirmed that cytopiloyne indeed inhibited Pdia4 activity (FIG. 5B).

The foregoing description of the exemplary embodiments of the invention has been presented only for the purposes of illustration and description and is not intended to be exhaustive or to limit the invention to the precise forms disclosed. Many modifications and variations are possible in light of the above teaching. The embodiments and examples were chosen and described in order to explain the principles of the invention and their practical application so as to enable others skilled in the an to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

All references cited and discussed in this specification are incorporated herein by reference in their entireties and to the same extent as if each reference was individually incorporated by reference.

What is claimed is:

1. A method for alleviating and/or treating diabetes and/or diabetes-related complications in a subject in need thereof, comprising:

administering to the subject in need thereof a therapeutically effective amount of a Pdia4 inhibitor to alleviate and/or treat diabetes and/or diabetes-related complications, wherein the diabetes-related complications are selected from the group consisting of eye disease, cardiovascular disease, kidney disease and foot ulcers, nephropathy, osteoporosis, skin ulcer, and eye damage, and the Pdia4 inhibitor is selected from the group consisting of

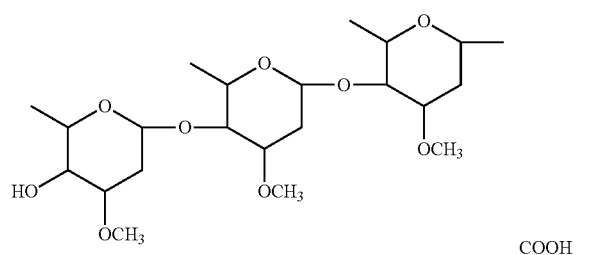

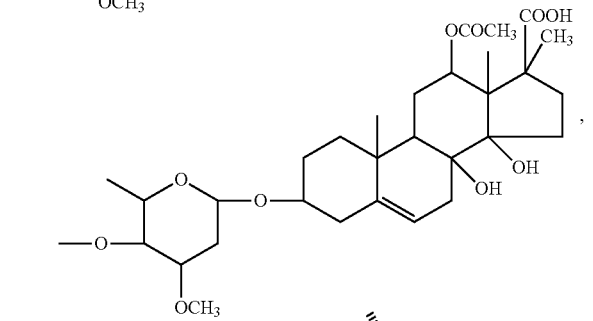

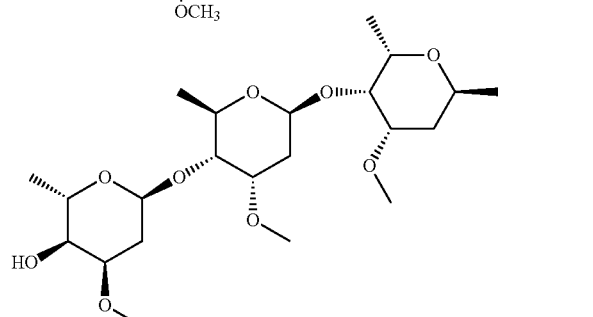

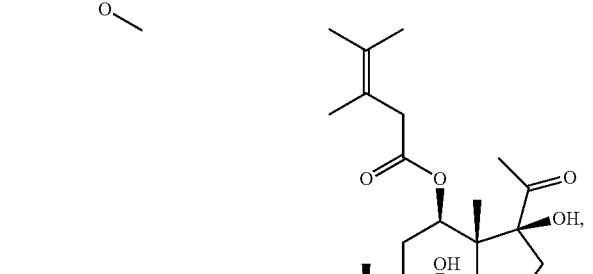

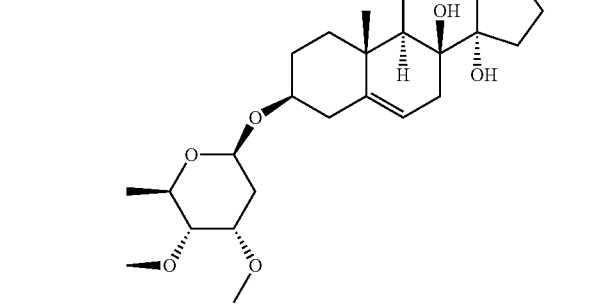

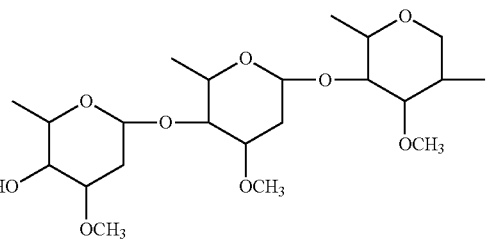

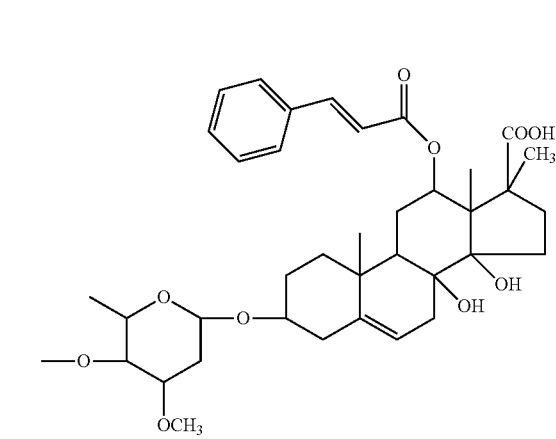

, and

-continued

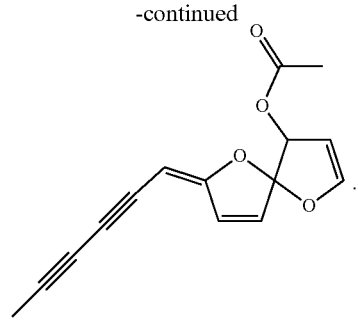

2. The method of claim 1, further comprising the steps of quantifying blood Pdia4 protein level in the subject before and after the administering step.

3. A method for returning blood glucose concentration to a normal level in a diabetic, comprising:

administering to the diabetic in need thereof a therapeutically effective amount of a Pdia4 inhibitor and a therapeutically effective amount of an insulin sensitizer to return the blood glucose concentration to the normal level in the diabetic wherein the Pdia4 inhibitor is a compound selected from the group consisting of

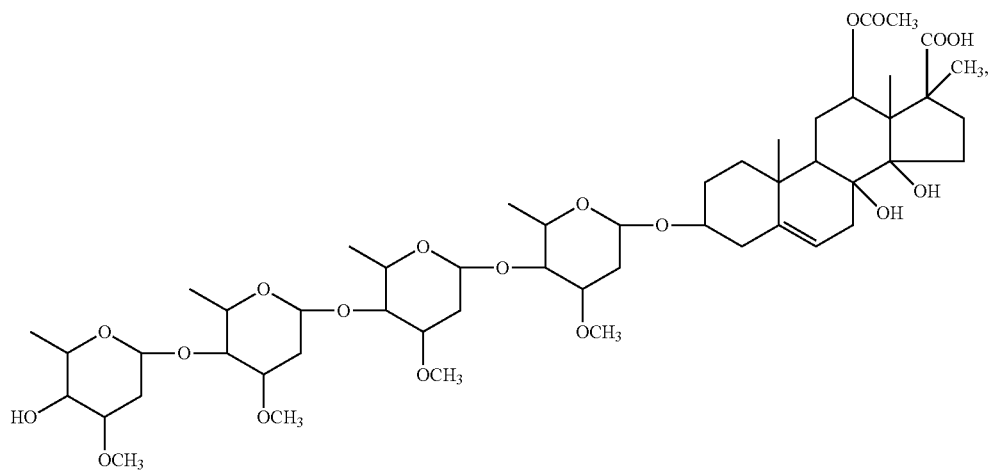

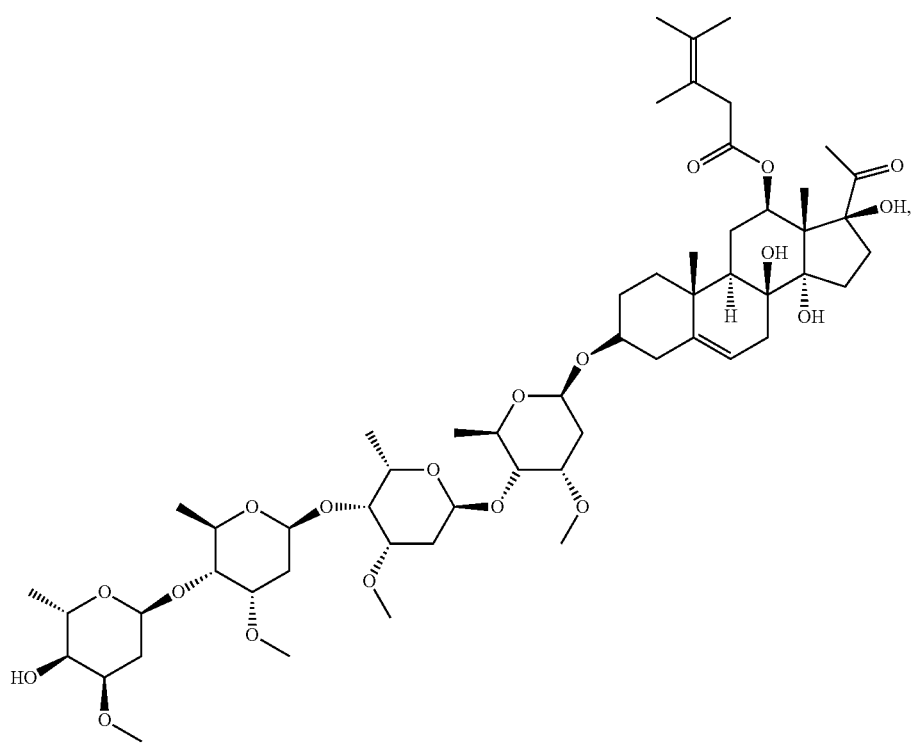

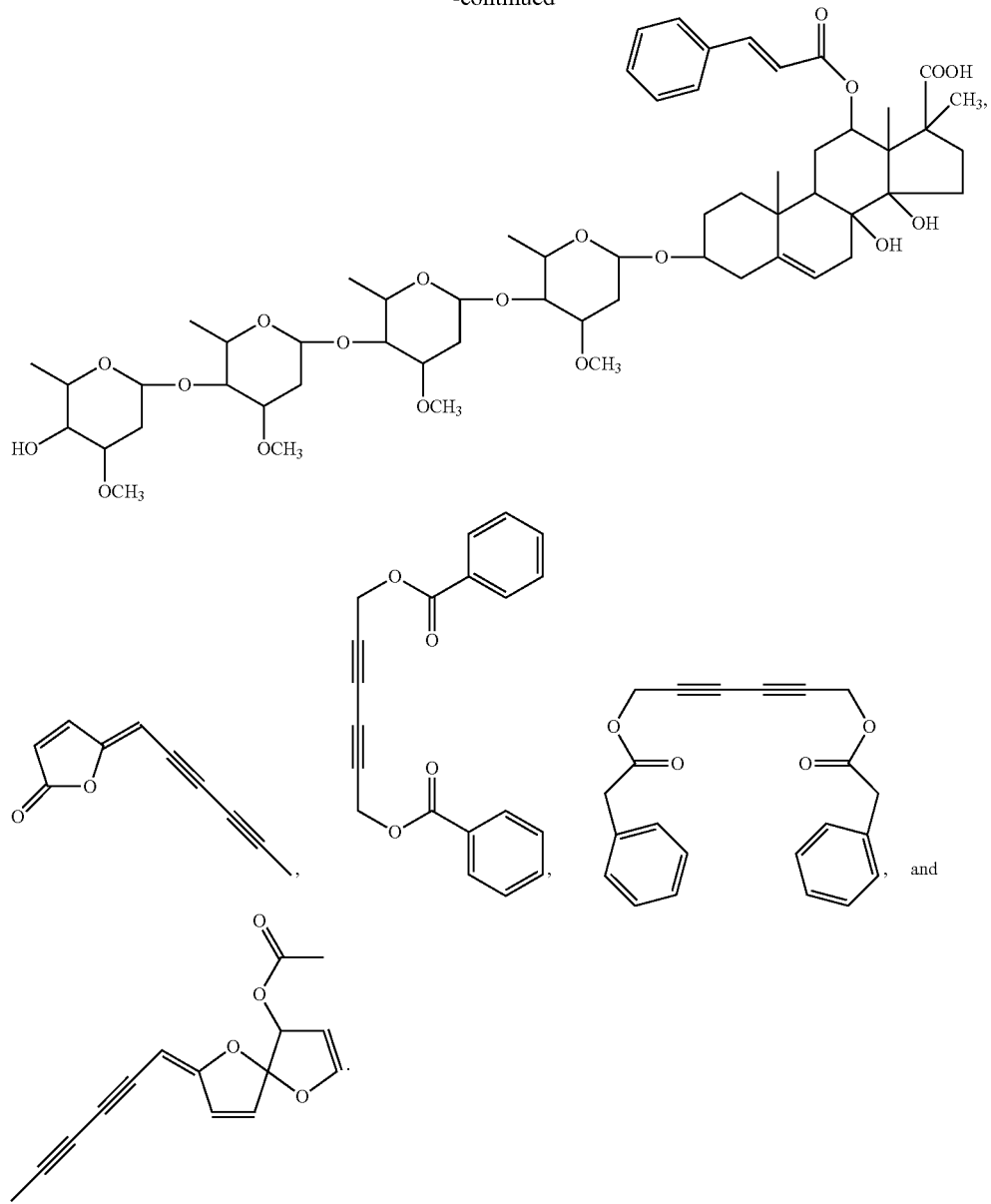

4. The method of claim 3, further comprising the steps of quantifying blood Pdia4 protein level in the diabetic before and after the administering step.

5. The method of claim 3, wherein the insulin sensitizer is metformin, rosiglitazone or a combination of metformin and rosiglitazone.

6. A method for returning blood glucose concentration to a normal level in a diabetic, comprising:
   administering to the diabetic in need thereof a therapeutically effective amount of a Pdia4 inhibitor and a therapeutically effective amount of an insulin sensitizer to return the blood glucose concentration to the normal level in the diabetic, wherein the Pdia4 inhibitor is shRNA comprising a nucleotide sequence selected from the group consisting of: SEQ ID NOs: 1 and 4.

7. The method of claim 6, wherein the insulin sensitizer is metformin, rosiglitazone or a combination of metformin and rosiglitazone.

8. The method of claim 6, further comprising the steps of quantifying blood Pdia4 protein level in the diabetic before and after the administering step.

* * * * *